US005640779A

United States Patent [19]
Rolloff et al.

[11] Patent Number: 5,640,779
[45] Date of Patent: Jun. 24, 1997

[54] APPARATUS, SYSTEM AND METHOD FOR FORMING CUSTOM-MADE SHOE INSERTS

[75] Inventors: Paul D. Rolloff, Fremont; Reginald T. Lamb, Redwood City, both of Calif.

[73] Assignee: Amfit Inc., Santa Clara, Calif.

[21] Appl. No.: 450,617

[22] Filed: May 25, 1995

Related U.S. Application Data

[63] Continuation of Ser. No. 305,831, Sep. 14, 1994, abandoned, which is a continuation of Ser. No. 167,560, Dec. 13, 1993, abandoned, which is a continuation of Ser. No. 12,259, Feb. 1, 1993, abandoned, which is a continuation of Ser. No. 909,162, Jul. 6, 1992, abandoned, which is a continuation of Ser. No. 819,386, Jan. 10, 1992, abandoned, which is a continuation of Ser. No. 716,661, Jun. 13, 1991, abandoned, which is a continuation of Ser. No. 627,587, Dec. 14, 1990, abandoned, which is a continuation of Ser. No. 425,933, Oct. 24, 1989, abandoned, which is a division of Ser. No. 34,077, Mar. 31, 1987, Pat. No. 4,876,758.

[51] Int. Cl.⁶ .............................. G01B 7/28; A41H 1/02; A61B 5/103
[52] U.S. Cl. .............................. 33/514.2; 33/552; 33/512; 12/142 N; 12/146 M; 12/1 R; 128/779
[58] Field of Search .............................. 33/514.2, 511, 33/512, 515, 504, 551, 552, 553, 554, 555, 557, 558, 560, 561; 12/142 N, 146 L, 146 M, 146 D, 146 C, 1 R; 128/779

[56] References Cited

U.S. PATENT DOCUMENTS

| 2,010,407 | 8/1935 | Matthias | 33/514.2 |
| 2,162,916 | 6/1939 | Hyland | 33/514.2 |
| 2,230,143 | 1/1941 | Hyland |  |
| 2,323,539 | 7/1943 | Hyland et al. | 12/142 N |
| 2,330,317 | 9/1943 | Stewart | 33/515 |
| 3,696,456 | 10/1972 | Dunham et al. | 12/146 L |
| 4,221,053 | 9/1980 | Bobel, II et al. | 33/552 |
| 4,400,884 | 8/1983 | Baresh et al. | 33/552 |
| 4,454,618 | 6/1984 | Curchod | 12/1 R |
| 4,517,696 | 5/1985 | Schwartz | 12/1 R |
| 4,679,331 | 7/1987 | Koontz | 33/551 |
| 4,817,222 | 4/1989 | Shafir | 12/146 L |

FOREIGN PATENT DOCUMENTS

| 281493 | 1/1915 | Germany | 33/514.2 |
| 596762 | 4/1934 | Germany . |  |
| 2308062 | 8/1973 | Germany . |  |
| 2821247 | 11/1979 | Germany . |  |
| 278299 | 10/1930 | Italy . |  |
| 172972 | 10/1934 | Switzerland . |  |
| 190837 | 5/1937 | Switzerland . |  |

OTHER PUBLICATIONS

CHIP Zeitschrift fur Mikrocomputer–Technik (1982) Dezember No. 12, Wuzburg, Deutschland T. Guss "Computer als Bildhauer" (pp. 36 & 37).

Primary Examiner—Christopher W. Fulton
Attorney, Agent, or Firm—Roland I. Griffin

[57] ABSTRACT

A foot impression unit is provided with an array of gauging elements, a control mechanism for urging the gauging elements into contact with the undersurface of a person's foot to form an impression of the undersurface of the foot, a locking mechanism for releasably locking the gauging elements in place to retain that impression, and a sensing mechanism for scanning the gauging elements to produce digital signals indicative of the positions of the gauging elements. These digital signals are stored and processed by a computer to provide a stored data record serving as a digital representation of the impression of the undersurface of the foot. The computer may also be employed to provide stored additional information for modifying that data record to compensate for a perceived defect of the foot. In response to the stored data record and any stored additional information for modifying that data record, a shaping unit shapes an insert blank to form a custom-made shoe insert conforming to the undersurface of the foot and compensating for any perceived defect of the foot.

13 Claims, 12 Drawing Sheets

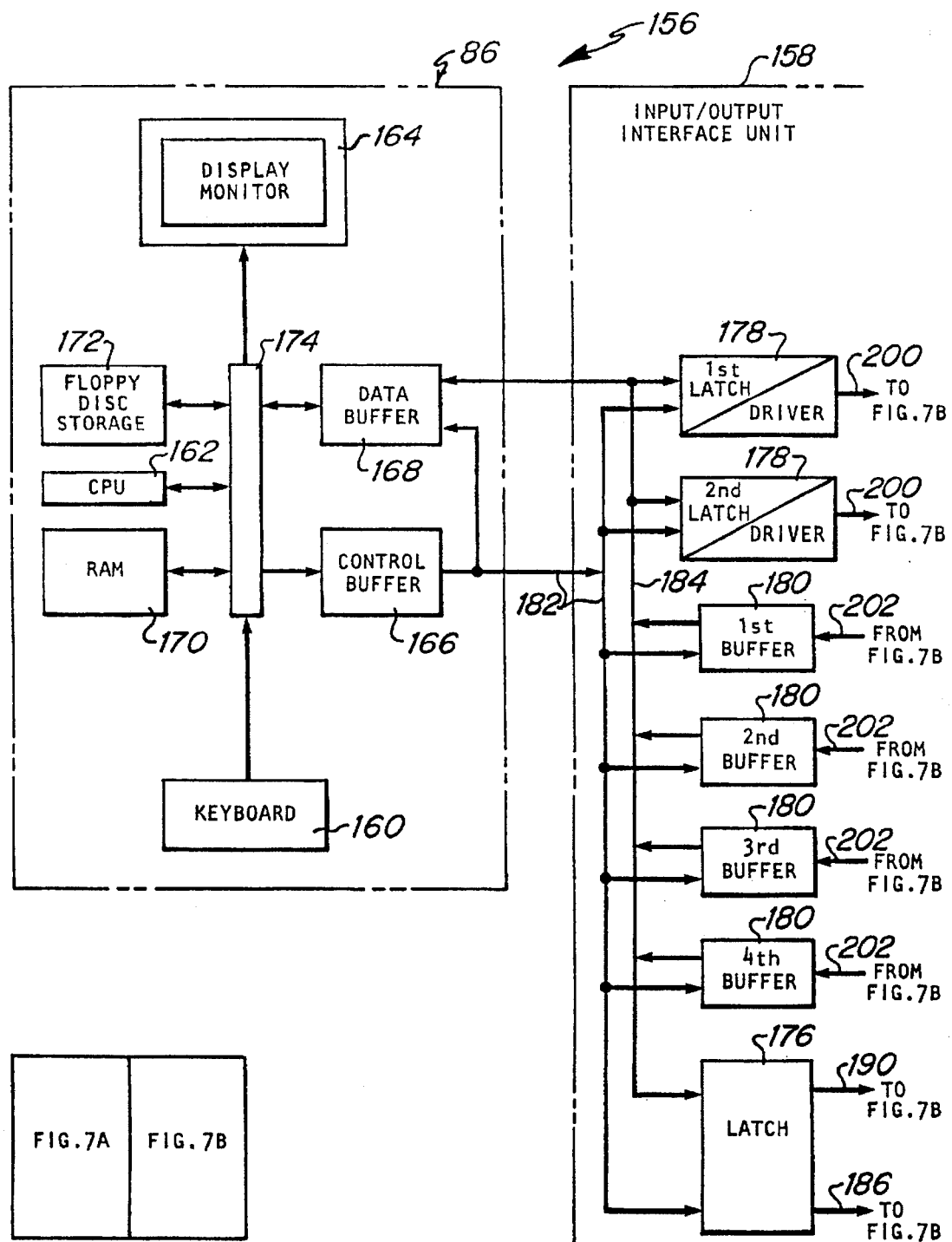

APPARATUS, SYSTEM AND METHOD FOR FORMING CUSTOM-MADE SHOE INSERTS

This is a continuation of application Ser. No. 08/305,831, filed Sep. 14, 1994 (abandoned), which is a continuation of application Ser. No. 08/167,560 filed Dec. 13, 1993 (abandoned), which is a continuation of application Ser. No. 08/012,259 filed Feb. 1, 1993 (abandoned), which is a continuation of application Ser. No. 07/909,162 filed Jul. 6, 1992 (abandoned), which is a continuation of application Ser. No. 07/819,386 filed Jan. 10, 1992 (abandoned), which is a continuation of application Ser. No. 07/716,661 filed Jun. 13, 1991 (abandoned), which is a continuation of application Ser. No. 07/627,587 filed Dec. 14, 1990 (abandoned), which is in turn a continuation of application Ser. No. 07/425,933 filed Oct. 24, 1989 (abandoned), which is a division of application Ser. No. 07/034,077 filed Mar. 31, 1987, and issued as U.S. Pat. No. 4,876,758 on Oct. 31, 1989.

BACKGROUND AND SUMMARY OF THE INVENTION

This invention relates generally to improvements in apparatus, systems and methods for forming custom-made shoe inserts conforming to a person's feet and/or compensating for defects of the person's feet. More particularly, this invention relates to an improved apparatus for digitizing the contour of the undersurface of a person's foot and to an improved system and method, employing such apparatus, for forming such custom-made shoe inserts.

Apparatus, systems and methods for forming custom-made shoe inserts conforming to a person's feet and/or compensating for defects of the person's feet are disclosed, for example, in U.S. Pat. No. 2,230,143 entitled METHOD AND APPARATUS FOR MAKING ORTHOPEDIC LIFTS (issued Jan. 28, 1941), in U.S. Pat. No. 4,454,618 entitled SYSTEM AND METHOD FOR FORMING CUSTOM-MADE SHOE INSERT (issued Jun. 19, 1984), and in U.S. Pat. No. 4,510,636 entitled SYSTEM AND METHOD FOR FORMING CUSTOM-MADE SHOE INSERTS (issued Apr. 16, 1985). In accordance with such apparatus, systems and methods a foot impression unit is employed for forming an impression of the undersurface of each foot. The foot impression unit includes a housing for supporting the foot, an array of pins supported by the housing for controlled movement to operative positions in contact with the undersurface of the foot (or a sheet of flexible material disposed between the array of pins and the foot) to form the impression, and a locking mechanism for thereupon locking the pins in place to retain the impression. Additionally, the foot impression unit may include provision for holding a foot with defects, such as pronation (an inward deflection of the foot), supination (an outward deflection of the foot), fallen arches or the like, in a corrected position while forming and retaining an impression corrected for such defects. A pivotally-mounted sensing and shaping unit is either manually or automatically driven laterally and to-and-fro across both the retained impression and an insert blank to mechanically sense the impression and to remove material from the blank in conformance with the sensed impression, thereby forming a custom-made shoe insert from the blank.

Since the custom-made shoe insert is formed with a foot supporting surface substantially conforming to the undersurface of the very foot for which the insert was formed, it provides better and more comfortable foot support than is provided by conventional insoles and standardized shoe inserts. Moreover if the custom-made shoe insert was formed from an impression corrected for foot defects, the custom-made shoe insert will tend to compensate for those defects. However, one disadvantage of the foregoing apparatus, systems and methods is that they have employed more expensive and less portable apparatus than desirable to facilitate their widespread adoption and usage in retail shoe stores, podiatrist's offices, and other such customer or patient service locations of the footware and footcare industries. This disadvantage is at least partly due to the fact that the foot impression unit has typically been combined and employed together with the sensing and shaping unit at each customer or patient service location or has been transported in its entirety from each such location, where an impression is formed and retained, to a central shaping location, where the sensing and shaping unit is used for mechanically sensing the impression retained by the foot impression unit and for shaping an insert blank in conformance with the sensed impression to form the custom-made shoe insert.

The aforementioned U.S. Pat. No. 2,230,143 discloses a foot impression unit that may be employed at each customer or patient service location to provide a manually recorded indication of each formed and retained impression upon a chart. In this foot impression unit at least some of the pins in successive rows of the array of pins have been provided with slots having camming surfaces for cooperating with corresponding camming surfaces of associated indicating elements (passing through those slots) to provide an indication of the displacements of those pins. Once the impression has been formed and retained, the indicating elements associated with each row of those pins are manually operated on a row-by-row basis to permit a set of curves indicative of the displacements of those pins to be manually drawn upon the chart along extended ends of the associated indicating elements. This chart is thereupon delivered to the central shaping location where the pins of another such foot impression unit are reset in accordance with the set of curves recorded on the chart and are locked in place to reform and retain the impression indicated by that set of curves. The sensing and shaping unit is then used to mechanically sense that reformed impression and shape an insert blank in conformance with the sensed reformed impression to form a custom-made shoe insert.

In theory the use of such a foot impression unit would obviate the need for transporting the foot impression unit from each customer or patient service location, where an impression is formed and recorded, to the central shaping location, where the recorded impression is reformed, retained and mechanically sensed to shape the blank and form the custom-made shoe insert. However, in practice one major disadvantage of using such a foot impression unit is the time and effort it would initially take at each customer or patient service location to successively manually draw the required set of curves upon the chart and the additional time and effort it would subsequently take at the central shaping location to manually reset the pins of another such foot impression unit in accordance with that set of curves to reform and retain the indicated impression. Another disadvantage is the unliklihood that the impressions formed, retained and manually recorded as sets of curves by different operators using any number of such foot impression units at any number of customer or patient service locations can be consistently and reliably reformed and retained by another operator using those sets of curves and skill another such foot impression unit at the central shaping location. To achieve any degree of consistency and reliability would require considerable training and skill on the part of every operator, as well as a great deal of precision in the construction of every foot impression unit to insure the required uniformity of operation from unit to unit. Still another disadvantage of using such a foot impression unit is that the required significant modification of the pins and use of cooperating manually-moveable indicating elements adds to the complexity and reduces the pin-packing density of the foot impression unit. This increases both the cost and the bulk of the foot impression unit, while decreasing the resolution and, hence, the quality of the impressions formed by the foot impression unit.

A system and method for forming a custom-made shoe last is disclosed in U.S. Pat. No. 3,696,456 entitled CUSTOM SHOE CONSTRUCTION SYSTEM (issued Oct. 10, 1972). Although not disclosed as being useful for forming custom-made shoe inserts, the last-mentioned system and method do employ the concept of obtaining and recording foot model data at a customer or patient service location and forming the custom-made shoe last from that data at a central shaping location. In accordance with that system and method a foot measuring unit, including three contour measuring blocks, is employed at the customer or patient service location to produce electrical analog signals indicative of the contour of the rear, side and upper surfaces of a person's foot. Each of the contour measuring blocks employs an array of pins concentrically attached to associated movable elements of associated tubular variable capacitors, which are arranged to produce electrical analog signals proportional to the positions of the tips of the pins with respect to fixed portions of the variable capacitors. A converter is also employed at the customer or patient service location to convert these electrical analog signals to digital foot model data and to store that data on a magnetic tape. This magnetic tape is subsequently delivered to the central shaping location where the digital foot model data stored on that magnetic tape and data previously used to produce custom-made shoe lasts and stored on another magnetic tape are initially compared by a computer to determine if a shoe last for a similar foot and desired shoe style has already been formed, thereby obviating the need to form a new shoe last. If a shoe last for a similar foot and desired style has not already been formed, the digital foot model data stored on the first-mentioned magnetic tape and the desired style model data stored on still another magnetic tape are combined by the computer to produce shoe-last information recorded on a punched tape. An automatic machine tool is then controlled by that punched tape to cut a custom-made shoe last from a wood blank in conformance with the recorded shoe-last information.

One disadvantage of the foregoing system and method for forming a custom-made shoe last, besides not being useful for forming a custom-made shoe insert, is that they employ a foot measuring unit for producing electrical analog signals indicative of the contour of the rear, side and upper surfaces of the foot and must therefore also employ a converter to process those analog signals and convert them to recorded digital foot model data. This adds to the cost and the bulk of the apparatus employed at each customer or patient service location to obtain and record such data. Another disadvantage of the foregoing system and method is that they do not provide for on-line modification of the recorded digital foot model data at the customer or patient service location to compensate for defects of the foot visually observed at that location. Another disadvantage of the foregoing system and method is that they do not provide for locking the pins of the foot measuring unit in place to retain an impression of the foot formed by those pins. This precludes a visual inspection of the impression formed by the pins of the foot measuring unit to verify the accuracy of the impression and to help in evaluating and discussing with the customer or patient what modification of the recorded foot model data might be most appropriate to compensate for defects of his or her foot. Still another disadvantage of the fore going system and method is that the attachment of the pins to the moving elements of tubular variable capacitors and the use of such tubular variable capacitors to determine the displacements of the pins adds to the complexity and reduces the pin-packing density of the contour measuring blocks. This increases both the cost and the bulk of the foot measuring unit, while decreasing the resolution and, hence, the quality of the impression formed by the foot impression unit.

An object of the various aspects of the present invention is to provide an improved apparatus, system and method for forming custom-made shoe inserts.

Another object of the various aspects of the present invention is to provide an improved apparatus, system and method, as in the last object, for overcoming the previously-mentioned and other disadvantages of the foregoing prior apparatus, systems and methods.

Another object of the various aspects of the present invention is to provide an improved apparatus, system and method, as in either of the last two objects, for facilitating more widespread adoption and usage of such apparatus, systems and methods and for thereby making custom-made shoe inserts more generally available to the public.

Another object of an aspect of the present invention is to provide an improved apparatus for digitizing the contour of a selected surface, such as the undersurface of a person's foot.

Another object of an aspect of the present invention is to provide less expensive, more portable, easier to use, and more reliable apparatus for digitizing the undersurface of a person's foot.

Another object of an aspect of the present invention is to provide an improved system, employing apparatus as in the last two objects, for forming an impression of the undersurface of a person's foot, scanning the impression to form a digital representation thereof, storing the digital representation, and forming a custom-made shoe insert from an insert blank in accordance with the stored digital representation.

Another object of an aspect of the present invention is to provide an improved system, as in the last object wherein the impression of the undersurface of the person's foot is formed and scanned at a customer or patient service location to form the digital representation of the impression, the digital representation is stored at the customer or patient service location and transmitted or sent to a shaping location, and the custom-made shoe insert is formed from the blank at the shaping location in accordance with the stored digital representation.

Another object of an aspect of the present invention is to provide an improved system, as in the last object, for making use of conventional computer equipment and techniques to control the forming and scanning of the impression of the undersurface of the person's foot, the forming and storing of the digital representation of the impression, the transmitting of the stored digital representation, and the forming of the custom-made shoe insert from the blank in accordance with the stored digital representation.

Another object of an aspect of the present invention is to provide an improved system and method for forming an impression of a person's foot (and, if desired, releasably retaining the impression to permit its inspection and evaluation), scanning the impression to form a digital representation of the impression, storing the digital representation, modifying the stored digital representation to compensate for a defect of the person's foot, and forming a custom-made shoe insert from a blank in conformance with the modified stored digital representation.

These and other objects, which will become apparent from a reading of this specification and an inspection of the accompanying drawings, are accomplished according to the preferred embodiment of the present invention by providing an improved foot impression unit and an improved system and method employing that foot impression unit to form custom-made shoe inserts as hereinafter described. This foot impression unit includes a frame for supporting a person's foot, an array of closely packed pins or gauging elements, an inflatable diaphragm, and a locking mechanism. The gauging elements are movably supported by the frame beneath the foot in spaced independently-guided relationship. Each gauging element includes a pair of permanent magnets disposed in opposing relationship at a predetermined intermediate location along the gauging element. The inflatable diaphragm is supported by the frame beneath the array of gauging elements and is inflated under control of a computer to yieldably urge the gauging elements into contact with the undersurface of the foot, thereby forming an impression of the undersurface of the foot. For purposes of the present invention the gauging elements are considered to be in contact with the undersurface of the foot even though a sheet of flexible material, a stocking, or the like should be disposed between the array of gauging elements and the foot. The locking mechanism is supported by the frame between adjacent rows of the gauging elements and may be operated under control of the computer to releasably lock the gauging elements in place and retain the impression of the undersurface of the foot.

In addition, the foot impression unit includes a sensing mechanism having a printed circuit board and an array of hall-effect sensors each mounted on the printed circuit board adjacent to a corresponding gauging element. The printed circuit board is supported by the frame for movement relative to the array of gauging elements under control of a stepper motor, which is in turn controlled by the computer. As the printed circuit board is stepped from its initial position to its final position and then back to its initial position, the array of hall-effect sensors scans the entire array of gauging elements at each discrete level to which the printed circuit board is stepped to produce digital signals indicative of the positions of the gauging elements. Each hall-effect sensor produces one binary digital signal when the printed circuit board is stepped to the discrete level or levels at which the permanent magnets of the corresponding gauging element are detected and another binary digital signal when the printed circuit board is stepped to every other discrete level. These digital signals are processed by the computer to provide a stored digital representation of the impression of the undersurface of the foot. The computer may be employed for modifying this stored digital representation in accordance with one or more visually-observed or measured defects of the foot to compensate for those defects.

A shaping unit is driven in accordance with the stored digital representation and any modifications thereof to remove material from an insert blank and form a custom-made shoe insert conforming to the under surface of the foot and/or compensating for defects of the foot. The shaping unit may comprise a milling machine having a rotary hemispherical cutter movable along X, Y and Z axes for removing material from the blank in accordance with the stored digital representation and any modifications thereof. This milling machine may be located at the same location as the foot impression unit and may be operated under control of the aforementioned computer, or it may be located at another location and operated under control of another computer. In the latter case, the stored digital representation may be transmitted from the aforementioned computer to the last-mentioned computer by employing conventional computer storage, networking or telecommunications equipment and techniques.

DESCRIPTION OF THE DRAWINGS

FIG. 7 is a figure map showing how FIGS. 7A and 7B fit together.

FIGS. 7A and 7B comprise a block diagram of a control system for use with the foot impression unit of FIGS. 1–6.

DESCRIPTION OF THE PREFERRED EMBODIMENT

Figure 1:
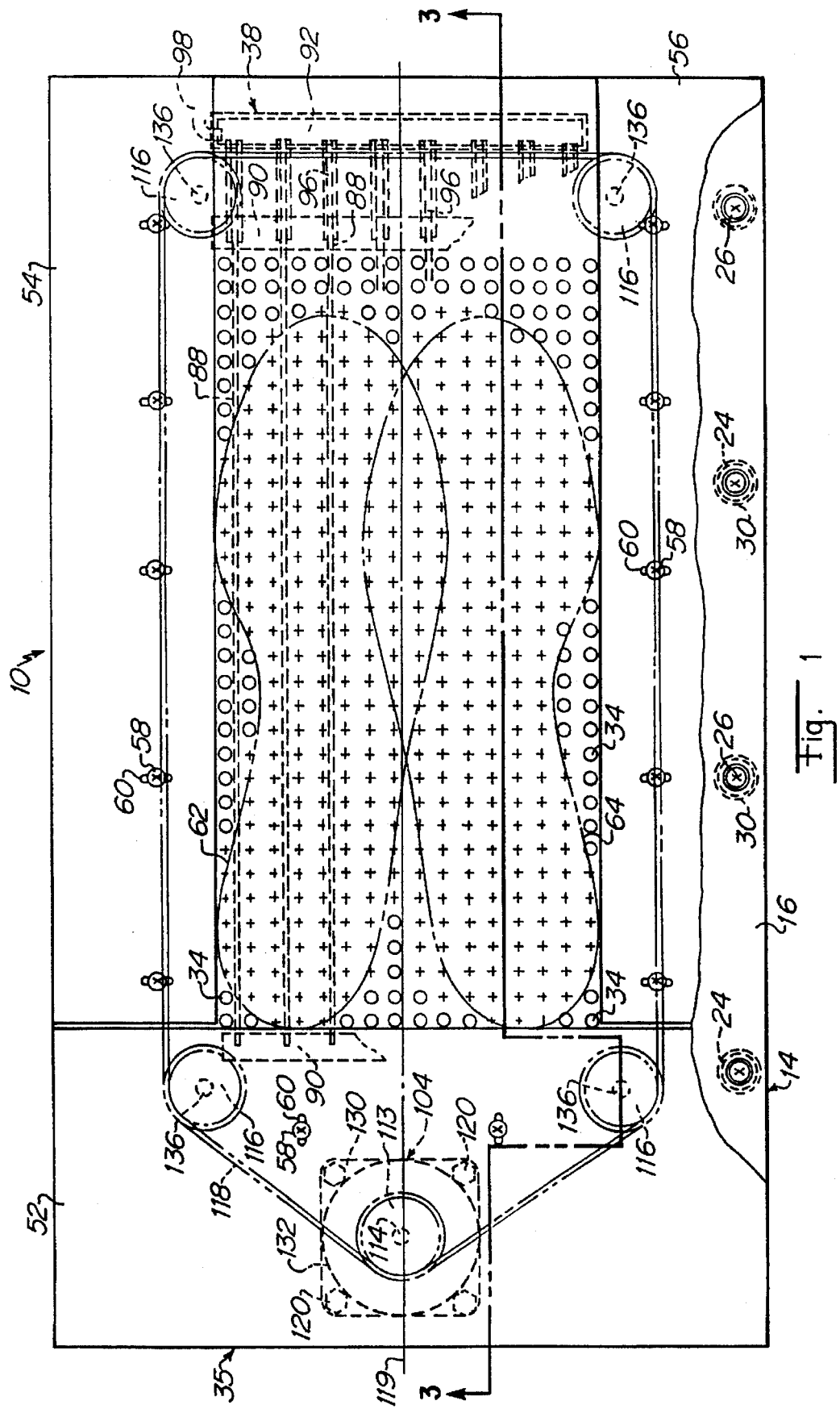
FIG. 1 is a partially cut-away top plan view of a foot impression unit in accordance with the preferred embodiment of the present invention.
Figure 2:
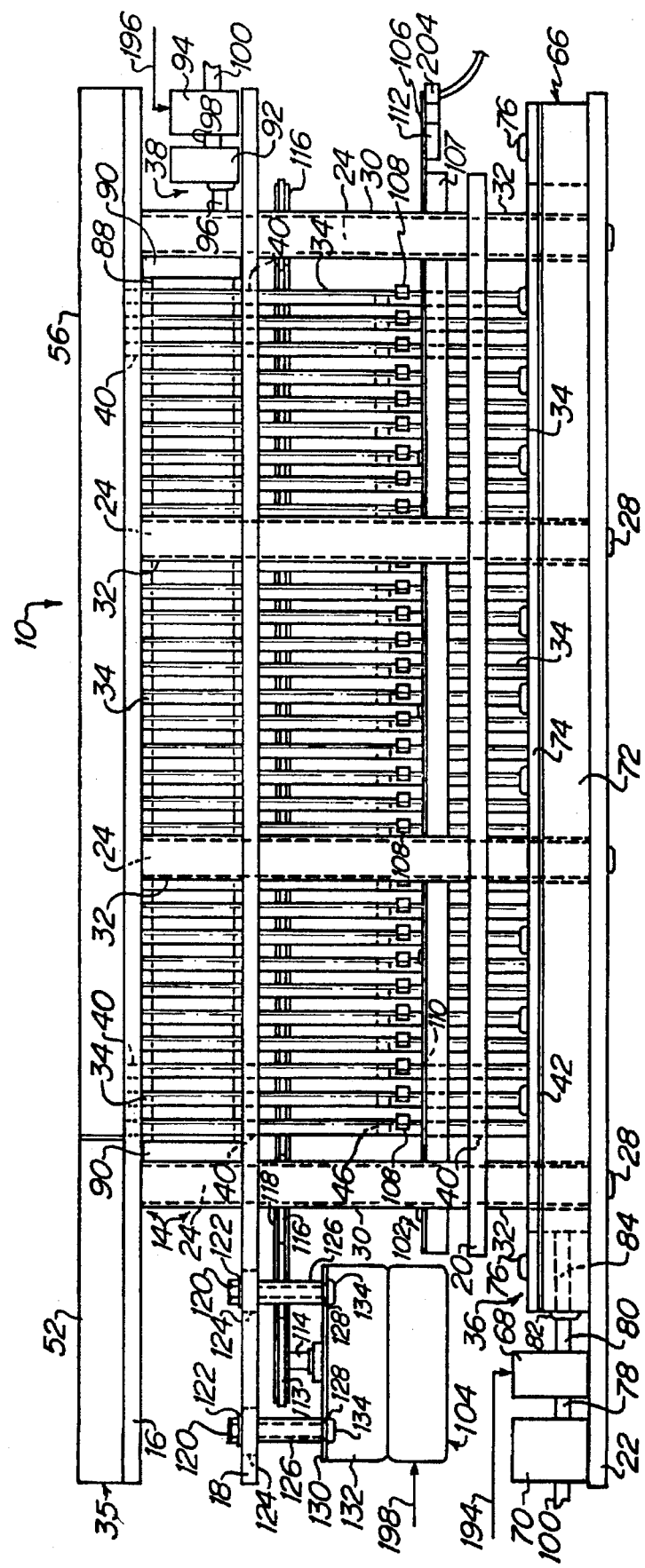
FIG. 2 is a side elevation view of the foot impression unit of FIG. 1.
Figure 3:
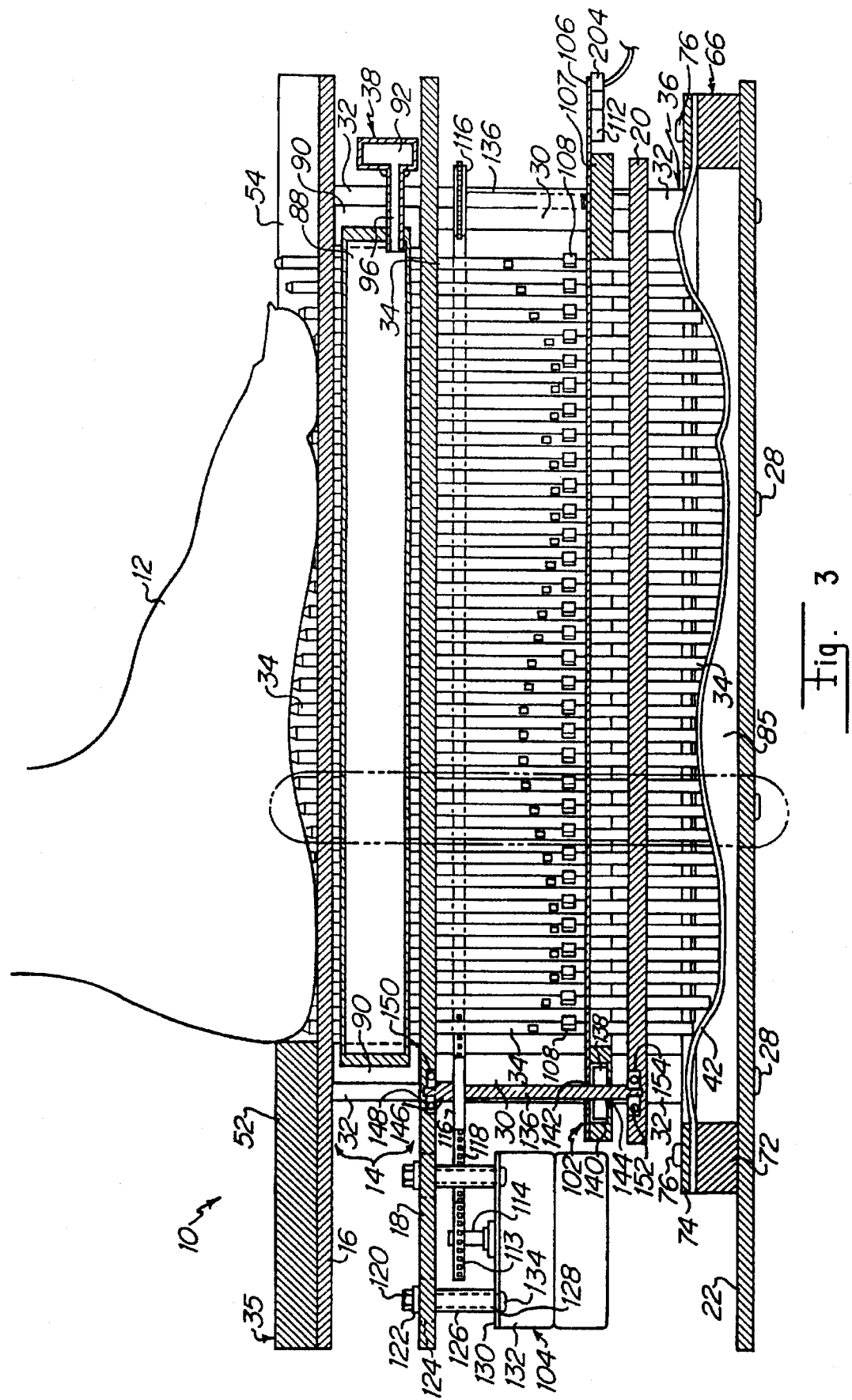
FIG. 3 is a cross-sectional side elevation view of the foot impression unit of FIGS. 1 and 2 taken along the line A—A in FIG. 1 and showing the foot impression unit being employed to form an impression of the undersurface of a person's foot.

Referring now to FIGS. 1–3, there is shown a foot impression unit 10 constructed in accordance with the preferred embodiment of the present invention and employed for digitizing the undersurface of a person's foot 12. The foot impression unit 10 includes a frame 14 having a top plate 16, intermediate plates 18 and 20, a bottom plate 22, and eight support posts 24 (four along each side of the foot impression unit). Top plate 16 is fixedly secured to the upper ends of support posts 24 by machine screws 26 seated in countersunk clearance holes in the top plate and screwed into threaded bore holes in the upper ends of the support posts. Bottom plate 22 is fixedly secured to the lower ends of support posts 24 by bolts 28 passing through clearance holes in the bottom plate and screwed into threaded bore holes in the lower ends of the support posts. The heads of bolts 28 serve as feet for supporting the foot impression unit 10 on the floor or any other desired platform. Support posts 24 pass through clearance holes in intermediate plates 18 and 20. These intermediate plates are spaced apart by spacer sleeves 30 coaxially disposed on support posts 24 between the intermediate plates and are fixedly held in place by spacer sleeves 32 coaxially disposed on the support posts between top plate 15 and intermediate plate 18 and between bottom plate 22 and intermediate plate 20.

The foot impression unit 10 also includes an array of gauging elements 34 for forming an impression of the undersurface of the foot 12, a guide 35 for properly positioning the foot with respect to the array of gauging elements, a control mechanism 36 for urging the gauging elements into contact with the undersurface of the foot to form the impression, and a locking mechanism 38 for locking the gauging elements in place to retain the impression so formed. Gauging elements 34 are closely packed and arranged in parallel rows and parallel columns orthogonally intersecting those rows (for example, with thirty-two gauging elements in each row and sixteen in each column, with the gauging elements having a center-to-center spacing of 0.32 inch, and with each gauging element having a diameter of 0.18 inch). Each gauging element 34 is vertically disposed within and individually guided for vertical movement by corresponding axially-aligned clearance holes 40 formed in top plate 16 and intermediate plates 18 and 20. The clearance holes 40 formed in top plate 16 are slightly larger than those formed in intermediate plates 18 and 20 so that gauging elements 34 are guided primarily by the corresponding axially-aligned clearance holes 40 formed in the intermediate plates and so that the top plate can be more easily put back in place if it should be removed to facilitate servicing of the locking mechanism 38. Gauging elements 34 are supported with their lower ends resting upon a rubber diaphragm 42 disposed on the upper surface of bottom plate 20 and with their upper ends lying in or slightly below the plane of the upper surface of top plate 16.

Figure 4:
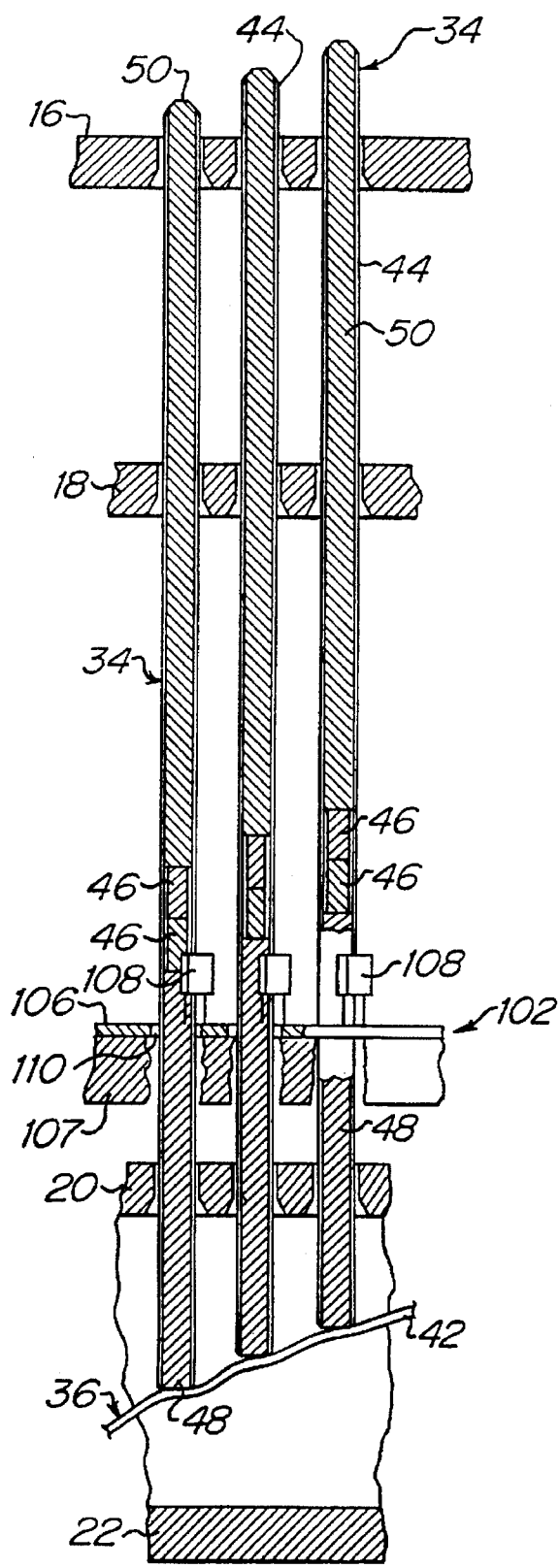
FIG. 4 is an enlarged cross-sectional side elevation view of a portion of the foot impression unit (the portion enclosed by the broken line in FIG. 3) with the sensing mechanism in its initial scanning position.
Figure 5:
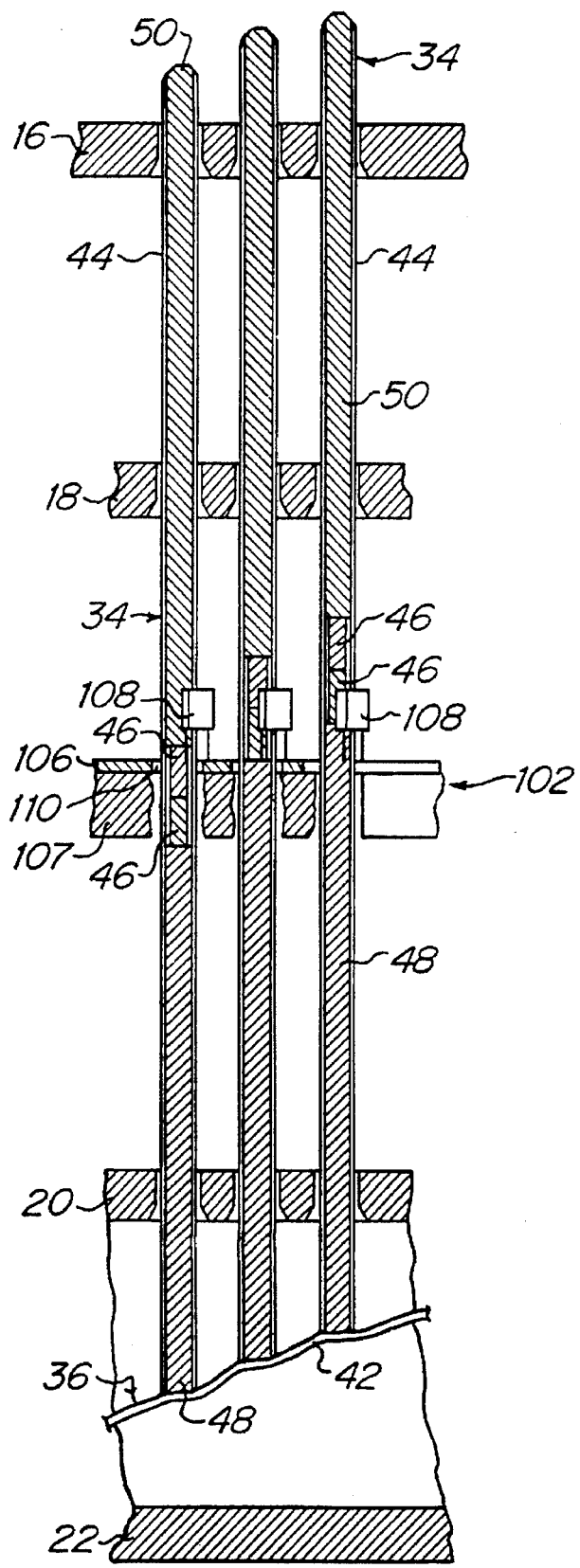
FIG. 5 is an enlarged cross-sectional side elevation view of the portion of the foot impression unit shown in FIG. 4, but with the sensing mechanism in an intermediate scanning position.
Figure 6:
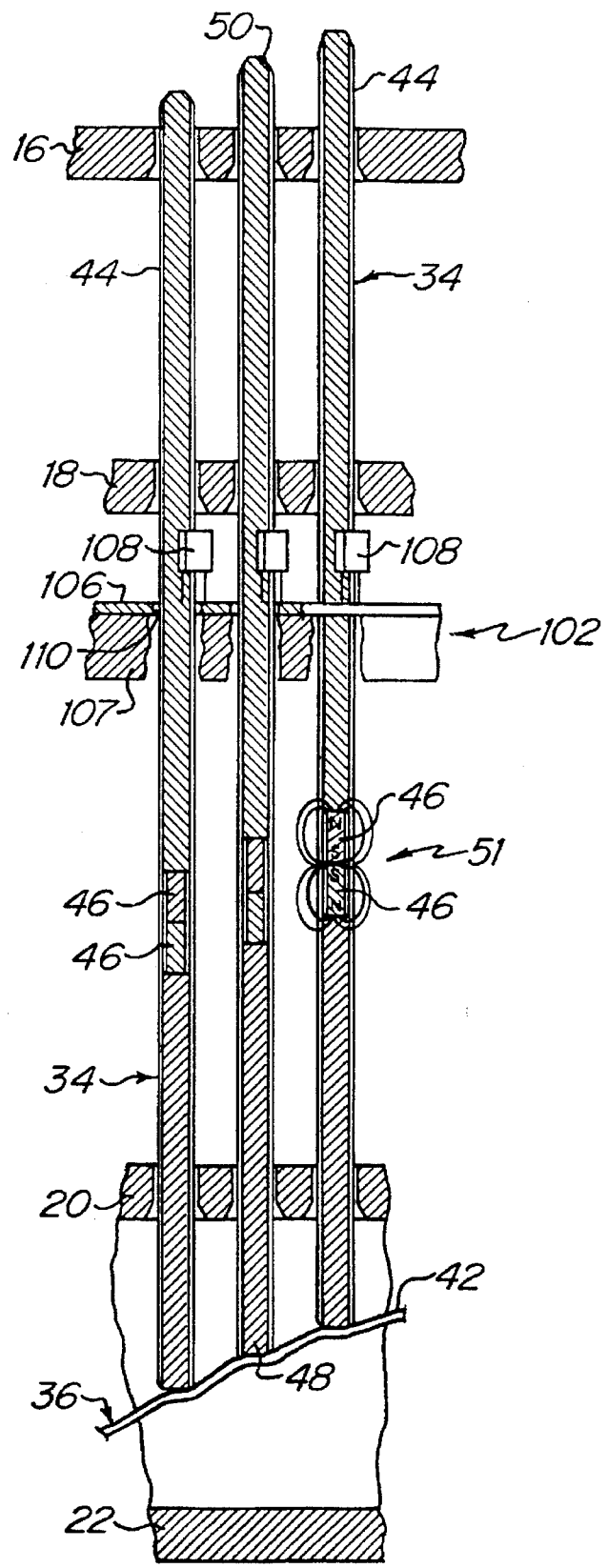
FIG. 6 is an enlarged cross-sectional side elevation view of the portion of the foot impression unit shown in FIGS. 4 and 5, but with the sensing mechanism in its final scanning position.

As best shown in FIGS. 4–6, each gauging element 34 comprises an elongated hollow cylindrical tube 44 having a pair of cylindrical permanent rod magnets 46, a cylindrical lower insert 48 and a cylindrical upper insert 50 disposed therein. The rod magnets 46 of each gauging element 34 are arranged with their south poles in abutting opposing relationship, as indicated in FIG. 6 where some of the field lines 51 are also shown for the magnets of one gauging element. Inserts 48 and 50 are employed to fixedly hold the rod magnets 46 of each gauging element 34 in place at a predetermined position within the corresponding tube 44. The predetermined position is selected such that the magnets 46 of each gauging element 34 will be disposed between intermediate plates 18 and 20 for any vertical position to which the gauging element may be moved by the control mechanism 36. Inserts 48 and 50 may simply be press fit into tubes 44 or may also be bonded thereto with an adhesive. Each lower insert 48 has a flat end protruding slightly from or flush with the lowermost end of the corresponding tube 44, while each upper insert 50 has a rounded or chamfered end protruding from the uppermost end of the corresponding tube.

Referring again to FIGS. 1–3, the guide 35 comprises an end guide member 52, a first side guide member 54, and a second side guide member 56 disposed directly adjacent to the left-hand end and the adjoining sides of the array of gauging elements 34. These guide members 52–56 are adjustably fixedly secured to top plate 16 by machine screws 58 passing through clearance slots 60 in the guide members and screwed into threaded bore holes in the top plate. This permits the guide members 52–56 to be secured in the proper positions with respect to the array of gauging elements 34. When an impression is to be formed of a person's right foot 12, that foot is positioned on top plate 16 with the heel of the foot resting against both the end guide member 52 and the first side guide member 54 and with the ball of the foot also resting against the first side guide member, as indicated in FIG. 1 by the dashed outline 62 of the foot. Similarly, when an impression is to be formed of the person's left foot 12, that foot is positioned on top plate 16 with the heel of the foot resting against both the end guide member 52 and the second side guide member 56 and with the ball of the foot also resting against the second side guide member, as indicated in FIG. 1 by the dashed outline 64 of the foot. The guide 35 may be used in this manner to properly position either the person's right or left foot 12 with respect to the array of gauging elements 34 while the gauging elements are employed for forming an impression of the undersurface of the foot. In addition, the guide 35 may be used to help support a foot 12 with defects, such as pronation, supination, fallen arches or the like, in a corrected position while the gauging elements 34 are employed for forming an impression corrected for such defects.

Referring particularly to FIGS. 2 and 3, the control mechanism 36 comprises rubber diaphragm 42, a rectangular retainer 66, a pneumatic valve 68, and an adjustable source of air pressure 70. Retainer 66 has a frame-like lower portion 72 and a mating frame-like upper portion 74 disposed around the array of gauging elements 34 and employed for retaining diaphragm 42 between bottom plate 22 and the array of gauging elements. The lower and upper portions 72 and 74 of retainer 66, together with a peripheral portion of diaphragm 42 clamped therebetween, are fixedly attached to bottom plate 22 by bolts 76. This captivates diaphragm 42 in air-tight engagement with retainer 66, which is in turn captivated in air-tight engagement with bottom plate 22. Diaphragm 42 and retainer 66 are formed and sized such that a central portion of the diaphragm normally rests upon the upper surface of bottom plate 22 beneath the array of gauging elements 34.

Figure 7B:
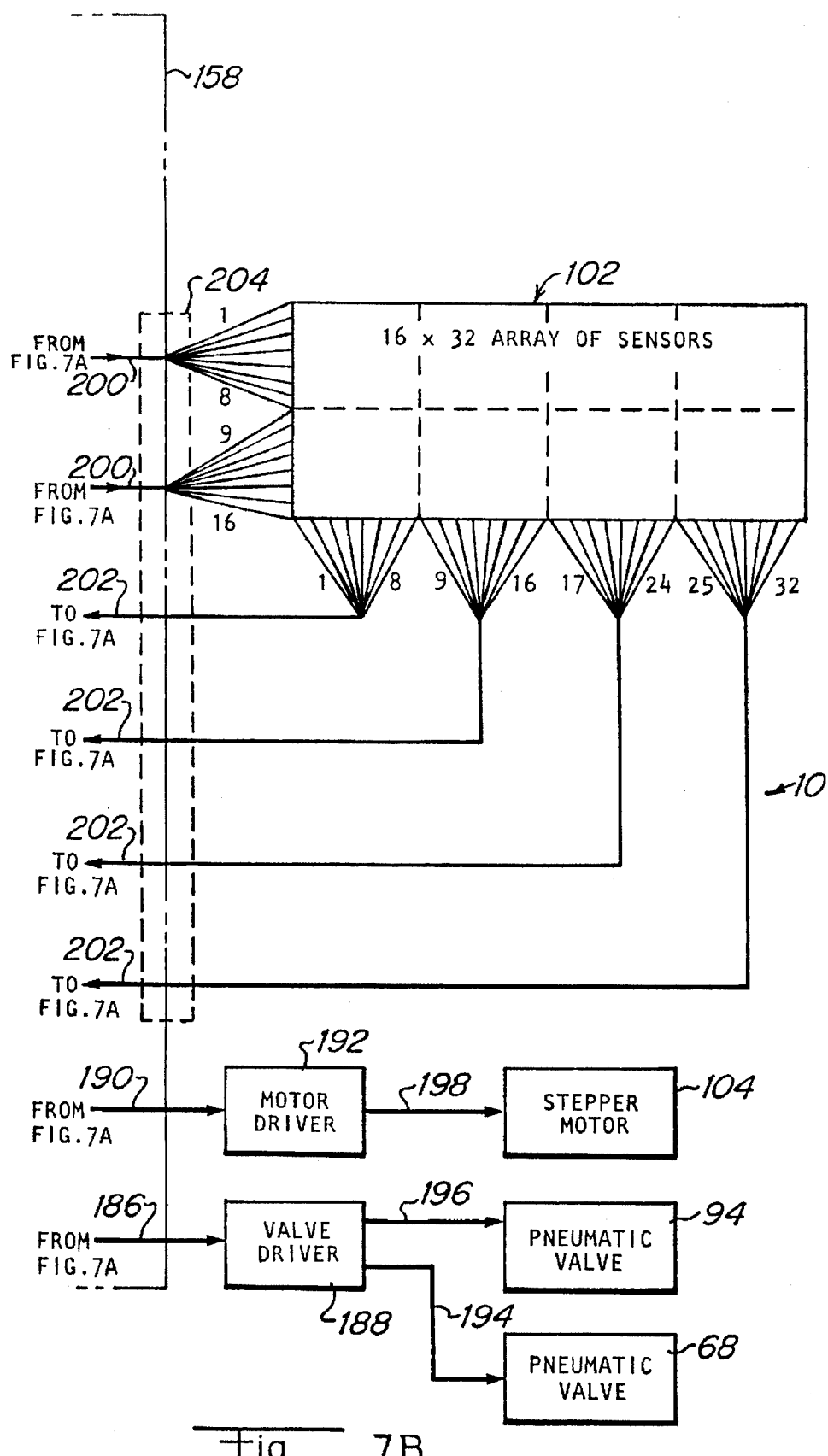

The adjustable source of air pressure 70 is coupled by a conduit 78 to the pneumatic valve 68, which is in turn coupled by a conduit 80 and an associated fitting 82 to a passageway 84 extending through the lower portion 72 of retainer 66. Under control of a computer 86 shown in FIG. 7, pneumatic valve 68 is actuated to connect the adjustable source of air pressure 70 to the conduit 80 and apply air pressure to the region 85 between bottom plate 22 and diaphragm 42. This inflates diaphragm 42 and yieldably urges gauging elements 34 into abutment with the under surface of the foot 12, thereby forming an impression of the undersurface of the foot as best shown in FIG. 3 for the person's left foot. Under control of computer 86, pneumatic valve 68 may subsequently be actuated to disconnect the adjustable source of air pressure 70 from conduit 80 and to vent that conduit to the atmosphere. This deflates diaphragm 42 and permits gauging elements 34 to return to their initial positions provided they are not locked in place by the locking mechanism 38.

Referring again to FIGS. 1–3, the locking mechanism 38 comprises a plurality of elongated inflatable tubes 88 of generally rectangular cross section, a pair of retainers 90, a manifold 92, a pneumatic valve 94 and the adjustable source of air pressure 70. For an array of gauging elements 34 consisting of sixteen rows and thirty-two columns, eight inflatable tubes 88 are employed with each inflatable tube being disposed between a corresponding different pair of the rows of gauging elements. The inflatable tubes 88 extend along the full length of the corresponding rows of gauging elements 34 between top plate 16 and intermediate plate 18 and are fixedly clamped at each end by retainers 90. These retainers 90 are in turn fixedly secured to top and intermediate plates 16 and 18 beyond the ends of the array of gauging elements 34 to hold the inflatable tubes 88 in place.

Each of the inflatable tubes 88 is coupled by an associated conduit 96 to manifold 92, which is in turn coupled by a conduit 98 to pneumatic valve 94. The adjustable source of air pressure 70 is also coupled to pneumatic valve 94 by a conduit 100. Under control of the computer 86 shown in FIG. 7, pneumatic valve 94 is actuated to connect the adjustable source of air pressure 70 to conduit 98 and apply air pressure to manifold 92 and, hence, to each of the inflatable tubes 88. This inflates the inflatable tubes 88 and forces the gauging elements 34 against the peripheral edges of the corresponding axially-aligned clearance holes 40 formed in intermediate plates 18 and 20, thereby locking the gauging elements in place. The locking mechanism 38 may be employed whenever it is desired to retain the impression of the undersurface of the foot 12 formed by the gauging elements 34. By retaining the impression in this manner, the impression may be visually inspected to verify its accuracy and to help in evaluating it and discussing with the customer or patient corrective measures to compensate for defects of his or her foot. Under control of computer 86, pneumatic valve 94 is subsequently actuated to disconnect the adjustable source of pressure 70 from conduit 98 and to vent that conduit to the atmosphere. This deflates manifold 92 and inflatable tubes 88, thereby unlocking gauging elements 34 and permitting them to return to their initial positions provided diaphragm 42 is deflated.

Referring particularly to FIGS. 2 and 3, the foot impression unit 10 further includes a sensing mechanism 102 for scanning the array of gauging elements 34 under control of the computer 86 and a stepper motor 104 and for producing digital signals indicative of the vertical positions of the gauging elements to provide a digital representation of the undersurface of the foot 12. This sensing mechanism 102 comprises a printed circuit board 106, an associated frame-like support plate 107 disposed around the array of gauging elements 34, and an array of hall-effect sensors 108 arranged in rows and columns corresponding to those of the array of gauging elements 34. Printed circuit board 106 is supported by the associated frame-like support plate 107 for vertical movement between intermediate plates 18 and 20 and is provided with clearance holes 110 axially aligned with the clearance holes 40 of top plate 16 and intermediate plates 18 and 20 for receiving gauging elements 34. Clearance holes 110 of printed circuit board 106 are somewhat larger than those of intermediate plates 18 and 20 so that vertical movement of the printed circuit board and its associated frame-like support plate will not interfere with gauging elements 34. The array of hall-effect sensors 108 is fixedly mounted on printed circuit board 106 with each hall-effect sensor disposed in an upright position directly adjacent to a corresponding gauging element 34. Each hall-effect sensor 108 is electrically connected by corresponding trace conductors formed on printed circuit board 106 to a female electrical connector 112 fixedly secured to the printed circuit board adjacent to an end portion thereof extending beyond support plate 107.

Once an impression of the undersurface of the foot 12 is formed by the array of gauging elements 34, stepper motor 104 is activated by computer 86 to step the sensing mechanism 102 vertically upward relative to the array of gauging elements from an initial position shown in FIG. 4 through a predetermined number of intermediate positions, as illustrated by the intermediate position shown in FIG. 5, to a final position shown in FIG. 6. Stepper motor 104 is thereupon activated by computer 86 to step the sensing mechanism 102 vertically downward relative to the array of gauging elements 34 from the final position back through the predetermined number of intermediate positions to the initial position. For example, the sensing mechanism 102 may be stepped vertically upward from its initial position a distance of 1.125 inches in 450 steps of 0.0025 inch per step to its final position and may thereupon be stepped vertically downward from its final position the same distance in the same number of steps back to its initial position.

In the initial position of the sensing mechanism 102, printed circuit board 106 and its associated support plate 107 are positioned adjacent to intermediate plate 20 such that hall-effect sensors 108 are disposed slightly below the positions occupied by magnets 46 of the corresponding gauging elements 34 when the gauging elements are in their initial positions, as shown in FIG. 2. Each succeeding upward step but the last moves the sensing mechanism 102 upward to a succeeding one of the predetermined intermediate positions. The last upward step moves the sensing mechanism 102 to its final position in which printed circuit board 106 and its associated support plate 107 are positioned adjacent to intermediate plate 18 such that hall-effect sensors 108 are disposed slightly below that intermediate plate. Each succeeding downward step but the last moves the sensing mechanism 102 downward to a succeeding one of the predetermined intermediate positions. The last downward step moves the sensing mechanism 102 back to its initial position.

Under control of computer 86, the array of hall-effect sensors 108 scans the entire corresponding array of gauging elements 34 at each position and, hence, at each discrete level of the sensing mechanism 102 to produce digital signals indicative of the operative positions of the gauging elements. Each hall-effect sensor 108 produces a binary "1" digital signal when the sensing mechanism 102 is in a position and, hence, at a discrete level at which the magnets 46 of the corresponding gauging element 34 are not detected by the hall-effect sensor. Concomitantly, each hall-effect sensor 108 produces a binary "0" digital signal when the sensing mechanism 102 is in a position and, hence, at a discrete level at which the magnets 46 of the corresponding gauging element 34 are detected by the hall-effect sensor (i.e., when the hall-effect sensor is at or near the south poles of the magnets). For example, when the sensing mechanism 102 is in its initial position, as shown in FIG. 4, or its final position, as shown in FIG. 6, every hall-effect sensor 108 will produce a binary "1" digital signal. However, when the sensing mechanism 102 is in an intermediate position, as shown in FIG. 5, some of the hall-effect sensors 108 (such as the left-most one shown in that figure) will produce a binary "1" digital signal, others (such as the right-most one shown in that figure) will produce either a binary "1" or "0" digital signal, and the remaining hall-effect sensors (such as the central one shown in that figure) will produce a binary "0" digital signal. The digital signals produced by the array of hall-effect sensors 108 at each position and, hence, at each discrete level of the sensing mechanism 102 are stored in and processed by computer 86 to provide a digital representation of the undersurface of the foot 12.

Referring once again to FIGS. 1–3, stepper motor 104 is coupled to sensing mechanism 102 by a sprocket wheel 113 fixedly attached to a drive shaft 114 of the stepper motor, by four sprocket wheels 116 coupled to support plate 107 of the sensing mechanism, and by a sprocket belt or chain 118 engaged with sprocket wheels 113 and 116. Stepper motor 104 is suspended from one end of intermediate plate 18 such that sprocket wheel 113 is disposed adjacent to intermediate plate 18 along a central axis 119 of the foot impression unit 10. Four mounting bolts 120 passing through corresponding washers 122, corresponding clearance slots 124 in intermediate plate 18, corresponding spacer sleeves 126, and corresponding clearance holes 128 in the four corners of a generally rectangular flange 130 of a housing 132 of stepper motor 104 are screwed into corresponding nuts 134 at the underside of flange 130 to fixedly hold the stepper motor in place.

The four sprocket wheels 116 are fixedly secured to the upper ends of four corresponding threaded shafts 136 and are disposed adjacent to intermediate plate 18 near the four corners of the array of gauging elements 34. As best shown in FIG. 3, the four threaded shafts 136 are in turn screwed into and through four corresponding mounting nuts 138 fixedly secured to support plate 107 of sensing mechanism 102 within four corresponding recesses 140 in the four corner portions of the support plate. Each threaded shaft 136 passes through a corresponding clearance hole 142 in printed circuit board 106 of sensing mechanism 102 and a corresponding clearance hole 144 in support plate 107. A hub portion 146 of the sprocket wheel 116 fixedly secured to the upper end of each threaded shaft 136 is rotatably supported by a corresponding ball bearing unit 148 fixedly secured to intermediate plate 18 within a corresponding recess 150 in that intermediate plate. Similarly, the lower end portion of each threaded shaft 136 is rotatably supported by a corresponding ball bearing unit 152 fixedly secured to intermediate plate 20 within a corresponding recess 154 in a corresponding corner portion of that intermediate plate.

As best shown in FIG. 1, sprocket belt or chain 118 is a continuous belt or chain that passes around and is engaged with sprocket wheel 113 and each of the four sprocket wheels 116. The tension with which sprocket belt or chain 118 is engaged with sprocket wheels 113 and 116 may be adjusted by loosening the four mounting bolts 120 supporting stepper motor 104, moving the stepper motor forward or backward along the central axis 119 of the foot impression unit 10 to adjust the tension of the sprocket belt or chain as desired, and tightening the mounting bolts 120 again to fixedly hold the stepper motor in place.

As best shown in FIG. 3, when stepper motor 104 is activated by computer 86 to step the sensing mechanism 102 upward, drive shaft 114 of the stepper motor rotates sprocket wheel 113 clockwise through a predetermined angle (for example, fifteen degrees) for each upward step. This in turn rotates sprocket belt or chain 118 and, hence, sprocket wheels 116 and the corresponding threaded shafts 136 clockwise, thereby moving the corresponding mounting nuts 138 and, hence, the sensing mechanism 102 vertically upward a predetermined distance (for example, 0.005 inch) for each upward step. Similarly, when stepper motor 104 is activated by computer 86 to step the sensing mechanism 102 downward, drive shaft 114 of the stepper motor rotates sprocket wheel 113 counter clockwise through the same predetermined angle for each downward step. This in turn rotates sprocket belt or chain 118 and, hence, sprocket wheels 116 and the corresponding threaded shafts 136 counterclockwise, thereby moving the corresponding mounting nuts 138 and, hence, the sensing mechanism 102 vertically downward the same predetermined distance for each downward step.

Referring now to FIGS. 6, 7, 7A and 7B there is shown a control system 156 for operating the foot impression unit 10 of FIGS. 1–6 and for storing and processing the digital signals produced by the array of hall-effect sensors 108 of the sensing mechanism 102 of the foot impression unit. Control system 156 includes computer 86 and an input/output interface unit 158 electrically connecting the computer to the foot impression unit 10. Computer 86 may comprise a conventional personal computer, such as an IBM PC compatible personal computer, having a keyboard input unit 160, a central processing unit (CPU) 162, a cathode ray tube display monitor 164, a control buffer unit 166, a data buffer unit 168, a random access memory (RAM) 170, and a floppy disc storage unit 172 all electrically interconnected by an internal bus 174. Keyboard input unit 160 is employed by an operator for entering instructions into computer 86 to operate the foot impression unit 10 as required to form an impression of the undersurface of the foot 12 and produce digital signals representative of that impression and to operate the computer as required to store and process those digital signals. In response to the entered instructions central processing unit 162 causes display monitor 164 to display messages indicating the current status of the foot impression unit 10 and prompting the operator regarding what is to be done next, causes control and data buffer units 166 and 168 and the input/output interface unit 158 to operate the foot impression unit 10 and sense the resulting digital signals representative of the impression formed of the undersurface of the foot 12, stores the sensed digital signals in the random access memory 170, and processes the stored digital signals to record a digital representation of that impression on a floppy disc of the floppy disc storage unit 172.

Input/output interface unit 158 includes a latch 176, first and second latch/driver circuits 178, first through fourth buffers 180, a control bus 182, and a data bus 184. Control buffer unit 166 of computer 86 is electrically connected to data buffer unit 168 of the computer and to latch 176, each latch/driver circuit 178, and each buffer 180 of input/output interface unit 158 by control bus 182. Data buffer unit 168 of computer 86 is electrically connected to latch 176, to each latch/driver circuit 178, and each buffer 180 of input/output interface circuit 158 by data bus 184. Latch 176 has a first output 186 electrically connected to a valve driver 188 and has a second output 190 electrically connected to a motor driver 192. Valve driver 188 has a first output 194 electrically connected to pneumatic valve 68 of the foot impression unit 10, as also shown in FIG. 2, to control the raising and lowering of the array of gauging elements 34 of the foot impression unit. In addition, valve driver 188 has a second output 196 electrically connected to pneumatic valve 94 of the foot impression unit 10, as also shown in FIG. 2, to control the locking and unlocking of the array of gauging elements 34. Motor driver 192 has an output 198 electrically connected to stepper motor 104, as further shown in FIG. 2, to control the upward and downward stepping of sensing mechanism 102 and, hence, of the array of hall-effect sensors 108 of the foot impression unit 10. Each latch/driver circuit 178 has an output 200 electrically connected to eight associated consecutive different rows of hall-effect sensors 108 employed for scanning eight corresponding rows of gauging elements 34 of the foot impression unit 10. Similarly, each buffer 180 has an output 202 electrically connected to eight associated consecutive different columns of hall-effect sensors 108 employed for scanning eight corresponding columns of gauging elements 34. The latch/ driver circuits 178 and buffers 180 are electrically connected to their associated rows and columns of hall-effect sensors 108 by a male electrical connector 204 plugged into the female electrical connector 112 as shown in FIGS. 2 and 3.

Initially the operator employs keyboard input unit 160 for entering into computer 86 an instruction to store specified information for identifying the person, etc. As a part of that instruction, the operator specifies the person's name, address, shoe size, and any other such pertinent information. In response to this instruction central processing unit 162 causes the specified information to be stored in random access memory 170.

Once the foregoing identification operation is completed, central processing unit 162 causes display monitor 164 to display a message indicating completion of that operation and prompting the operator to enter the next instruction into computer 86. At this point the person's right foot 12 is properly positioned on the foot impression unit 10, as previously explained and as shown in FIG. 1. The operator then employs keyboard input unit 160 for entering into computer 86 an instruction to raise the array of gauging elements 34. In response to this instruction central processing unit 162 causes control buffer unit 166 to activate data buffer unit 168 for transmitting control data and to activate latch 176 for receiving control data from the data buffer unit. Central processing unit 162 also causes activated data buffer unit 168 to transmit control data to activated latch 176 as required to set that latch for controlling valve driver 188 to activate pneumatic valve 68 and raise the array of gauging elements 34. This urges gauging elements 34 into contact with the undersurface of the person's right foot 12 to form an impression of the under surface of that foot, as previously explained and as shown for the person's left foot in FIG. 3.

Once the foregoing impression-forming operation is completed, central processing unit 162 causes display monitor 164 to display a message indicating completion of that operation and prompting the operator to enter the next instruction into computer 86. The operator may then employ keyboard input unit 160 for entering into computer 86 an instruction to lock the array of gauging elements 34 in place. In response to this instruction central processing unit 162 again causes control buffer unit 166 to activate data buffer unit 168 for transmitting control data and to activate latch 176 for receiving control data from the data buffer unit. Central processing unit 162 also causes activated data buffer unit 168 to transmit control data to activated latch 176 as required to set that latch for controlling valve driver 188 to activate pneumatic valve 94 and to subsequently deactivate pneumatic valve 68. The activation of pneumatic valve 94 locks the array of gauging elements 34 in place and thereby retains the impression formed of the undersurface of the person's right foot by the gauging elements, while the deactivation of pneumatic valve 68 permits the array of gauging elements to return to its initial position whenever it is subsequently unlocked.

Once the foregoing locking operation is completed, central processing unit 162 causes display monitor 164 to display a message indicating completion of that operation and prompting the operator to enter the next instruction into computer 86. The operator may then employ keyboard input unit 160 for entering into computer 86 an instruction to scan the array of gauging elements 34. In response to this instruction central processing unit 162 initially causes control buffer unit 166 to activate data buffer unit 168 for transmitting control data, to activate the first latch/driver circuit 178 for receiving control data from the data buffer unit, and to activate the first buffer 180 for sensing digital signals produced by its associated eight columns of hall-effect sensors 108. Central processing unit 162 also causes activated data buffer unit 168 to transmit control data to the activated first latch/driver circuit 178 as required for setting that latch/driver circuit to activate its first associated row of hall-effect sensors 108. This causes each hall-effect sensor 108 in the activated first row of hall-effect sensors to produce a digital signal as previously described in connection with FIGS. 1–6.

The digital signals produced by the first eight hall-effect sensors 108 in the activated first row of hall-effect sensors are sensed by the activated first buffer 180. Central processing unit 162 next causes control buffer unit 166 to activate data buffer unit 168 for receiving those eight sensed digital signals from the activated first buffer 180, and causes the eight sensed digital signals so received to be stored in random access memory 170. These eight sensed digital signals are stored to record the results of scanning the first eight gauging elements 34 in the first row of gauging elements at the initial position of the sensing mechanism 102 of the foot impression unit 10.

Central processing unit 162 then causes control buffer unit 166 to deactivate the first buffer 180 and to activate the second buffer 180 for sensing the digital signals produced by its associated eight columns of hall-effect sensors 108 (i.e., the digital signals produced by the next eight hall-effect sensors in the activated first row of hall-effect sensors). Concomitantly, central processing unit 162 causes control buffer unit 166 to activate data buffer unit 168 for receiving the eight sensed digital signals from the activated second buffer 180, and causes those eight sensed digital signals so received to be stored in random access memory 170. This process is repeated for each succeeding buffer 180. In this manner thirty-two sensed digital signals are stored to record the results of scanning the entire first row of gauging elements 34 at the initial position of the sensing mechanism 102 of the foot impression unit 10.

Once all of the digital signals produced by the first activated row of hall-effect sensors 108 have been sensed and stored, central processing unit 162 repeats the foregoing row-scanning process as required for setting the first latch/ driver circuit 178 to sequentially activate each succeeding associated row of hall-effect sensors 108 (in place of the preceding row) and, while each succeeding associated row of hall-effect sensors is activated, to store thirty-two sensed digital signals in random access memory 170. This records the results of scanning each corresponding row of gauging elements 34 at the initial position of the sensing mechanism 102 of the foot impression unit 10. Central processing unit 162 thereupon repeats the row-scanning process as required for setting the second latch/driver circuit 178 to sequentially activate each succeeding associated row of hall-effect sensors 108 (in place of the preceding row) and, while each succeeding associated row of hall-effect sensors is activated, to store thirty-two sensed digital signals in random access memory 170 and thereby record the results of scanning the corresponding row of gauging elements 34 at the initial position of the scanning mechanism 102.

Upon completion of the scanning of the entire array of gauging elements 34 at the initial position of the sensing mechanism 102 of the foot impression unit 10, central processing unit 162 causes control buffer unit 166 to activate data buffer unit 168 for transmitting control data and to activate latch 176 for receiving control data from the data buffer unit. Central processing unit 162 also causes activated data buffer unit 168 to transmit control data to activated latch 176 as required for controlling motor driver 192 and, hence, stepper motor 104 to step the sensing mechanism 102 upward to its first intermediate position. This stepping process is repeated by central processing unit 162 as required to sequentially step the sensing mechanism 102 upward to each succeeding intermediate position and thence to its final position. Central processing unit 162 thereupon repeats the stepping process as required for controlling motor driver 192 and, hence, stepper motor 104 to sequentially step the sensing mechanism 102 downward from its final position to each succeeding intermediate position and thence back to its initial position.

While the sensing mechanism 102 is in each position as it is being stepped upward, central processing unit 162 repeats the above-described row-scanning process as required to store in random access memory 170 the sensed digital signals produced by each row of hall-effect sensors 108 at each position and thereby record the results of scanning each corresponding row of gauging elements 34 at each position. Similarly, while the sensing mechanism 102 is in each position as it is being stepped downward, central processing unit 162 also repeats the above-described row-scanning process as required to store in random access memory 170 the sensed digital signals produced by each row of hall-effect sensors 108 at each position and thereby again record the results of scanning each corresponding row of gauging elements 34 at each position. Each hall-effect sensor 108 detects the magnets 44 of the corresponding gauging element 34 at several successive positions while the sensing mechanism 102 is being stepped upward and at several successive positions while the sensing mechanism is being stepped downward. Moreover, the successive positions at which the magnets 44 of the corresponding gauging element 34 are detected while the sensing mechanism 102 is being stepped upward may differ from the successive positions at which those magnets are detected while the sensing mechanism is being stepped downward due to hall-effect hysteresis characteristics. As previously explained, each hall-effect sensor 108 produces a binary "0" digital signal at each position in which the magnets 44 of the corresponding gauging element 34 are detected and a binary "1" digital signal at each remaining position. Thus, a binary "0" digital signal is stored in random access memory 170 for each successive position at which each hall-effect sensor 108 detects the magnets 44 of the corresponding gauging element, and a binary "1" digital signal is stored for every remaining position.

Following the upward stepping of sensing mechanism 102, central processing unit 162 averages the successive positions at which each hall-effect sensor 108 has detected the magnets 44 of the corresponding gauging element 34 and for which a binary "0" digital signal has been stored in random access memory 170 during upward stepping and stores in the random access memory a digital signal indicative of the level of this first determined average position relative to the level of the initial position of the sensing mechanism. Similarly, following the downward stepping of sensing mechanism 102, central processing unit 162 averages the successive positions at which each hall-effect sensor 108 has detected the magnets 44 of the corresponding gauging element 34 and for which a binary "0" digital signal has been stored in random access memory 170 during downward stepping and stores in the random access memory a digital signal indicative of the level of this second determined average position relative to the level of the initial position of the sensing mechanism. Central processing unit 162 thereupon averages the first and second determined average positions for each hall-effect sensor 108 and stores in random access memory 170 a digital signal indicative of the level of the finally-determined average position relative to the level of the initial position of sensing mechanism 102. The level of the finally-determined average position may lie half way between two successive positions of the sensing mechanism 102.

This completes the scanning operation and provides a stored data record of the digital signals indicative of the levels at which all of the hall-effect sensors 108 are finally determined to have detected the magnets 44 of the corresponding gauging elements 34 relative to the level of the initial position of sensing mechanism 102 and, hence, of the levels or heights of the corresponding gauging elements relative to the upper surface of top plate 16. The stored data record so provided accordingly serves as a digital representation of the impression formed of the undersurface of the person's right foot by gauging elements 34 and defines a custom-made shoe insert 206, as shown, for example, in FIG. 8, conforming to the undersurface of that foot.

It should be noted that in the process of averaging the first and second determined average positions for each hall-effect sensor 108 central processing unit 162 subtracts the level of a previously-determined calibration reference average position for the same hall-effect sensor relative to the initial position of sensing mechanism 102 from the sum of the levels of the first and second determined average positions before dividing that sum by two to obtain the level of the finally-determined average position. A reference record of digital signals indicative of the levels of the calibration reference average positions for all of the hall-effect sensors 108 is obtained and stored in random access memory 170 and on a floppy disc for this purpose during a calibration operation performed before initially putting the foot impression unit 10 into service. The calibration operation is performed by placing a flat reference plate over the entire array of gauging elements 34, by performing the foregoing impression-forming operation to urge the array of gauging elements 34 into contact with the flat reference plate, by thereupon performing the foregoing locking operation to releasably lock the array of gauging elements in place, by then performing the foregoing scanning operation to store in random access memory 170 the reference record of the digital signals indicative of the levels of the calibration reference average positions at which all of the hall-effect sensors 108 are finally determined to have detected the magnets 44 of the corresponding gauging elements, and by thereafter performing a recording operation (hereinafter described) to record the reference record on a floppy disc from which the reference record may be recalled to the random access memory whenever necessary.

Employing the calibration operation and the resulting reference record in this manner eliminates the necessity of mounting the magnets 44 of the gauging elements 34 and the hall-effect sensors 108 of the sensing mechanism 102 with great precision, eliminates the necessity of otherwise forming the gauging elements with great precision, and eliminates or accounts for hall-effect hysteresis characteristics. This enables the foot impression unit 10 to be fabricated at substantially less cost. Moreover, the calibration operation can be performed periodically after the foot impression unit 10 is put into service to check and, if necessary, recalibrate the foot impression unit by obtaining and storing a new reference record.

Once the foregoing scanning operation is completed, central processing unit 162 causes display monitor 164 to display a message indicating completion of that operation and prompting the operator to enter the next instruction into computer 86. The operator may then employ keyboard input unit 160 for entering into computer 86 an instruction to store in random access memory 170 additional information for modifying the stored data record as may be desired to compensate for one or more defects of the person's right foot. Any such defects may be detected and the required modifications of the stored data record determined by visual inspection of the person's right foot, by visual inspection of the impression formed of the undersurface of that foot by the gauging elements 34, and by employing apparatus and techniques generally used in podiatry for this purpose. For example, an instruction may be entered into computer 86 to store in random access memory 170 additional information for modifying the stored data record by effecting a pronation (eversion) ramp correction, a supination (inversion) ramp correction, an insert thickness adjustment, a pad/depression selection and placement adjustment, an overall arch support adjustment, a heel lift ramp adjustment, a toe crest or sulcus limit adjustment, or an insert length adjustment. Moreover, instructions may be entered into computer 86 to effect any one or more of these modifications for either the right or the left foot (or both feet) and to specify to what extent any one or more of these modifications shall be effected.

Figure 8:
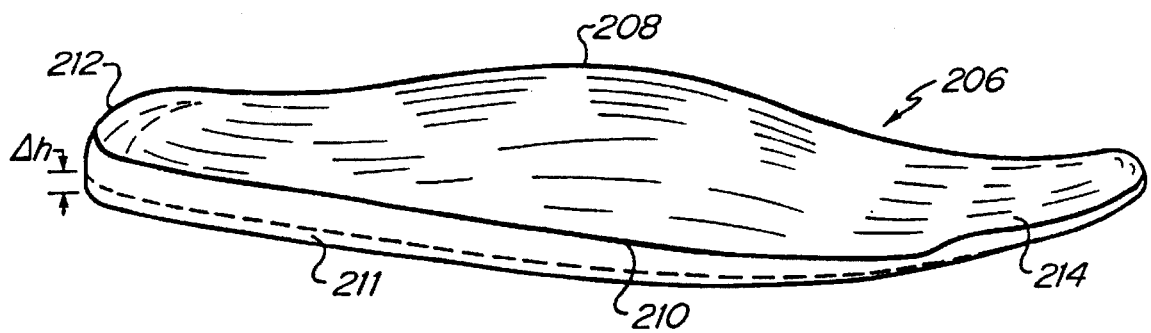
FIG. 8 is a perspective view of a custom-made shoe insert formed in accordance with the present invention.

The pronation (eversion) ramp correction compensates for either the right or the left foot (or both feet) falling inward towards the center of the person's body (as in the case of a collapsed arch) by modifying the stored data record as required to increase the support provided across the custom-made shoe insert 206 of FIG. 8 in a ramp-like manner from a maximum increase at the inside (or arch side) 208 of the insert to no increase at the outside 210 of the insert. This provision of increased support for the inside of the foot is referred to as posting the first metatarsal if applied to the metatarsal region of the foot and as wedging the heel if applied to the heel region of the foot. As part of the instruction for initiating the pronation (eversion) ramp correction, the operator specifies the desired maximum increase in the height of the custom-made shoe insert 206 at the inside 208 of the insert (this specified maximum height increase may be, for example, in the range of from one-sixteenth to six-sixteenths of an inch) and specifies the area of the ramp correction (this specified area may range from a localized portion of the support surface of the insert to the entire support surface). In response to this instruction central processing unit 162 determines the required ramp correction from the specified maximum height increase at the inside 208 of the custom-made shoe insert 206 to a zero increase at the outside 210 of the insert and stores in random access memory 170 additional information for modifying the stored data record in the specified area in accordance with the required ramp correction.

The supination (inversion) ramp correction compensates for either the right or the left foot(or both feel falling outward away from the center of the person's body by modifying the stored data record as required to increase the support provided across the custom-made shoe insert 206 of FIG. 8 in a ramp-like manner from a maximum increase at the outside 210 of the insert to no increase at the inside (or arch side) 208 of the insert. This provision of increased support for the outside of the foot is referred to as posting the fifth metatarsal if applied to the metatarsal region and as wedging the heel if applied to the heel region. As part of the instruction for initiating the supination (inversion) ramp correction, the operator specifies the desired maximum increase in the height of the custom-made shoe insert 206 at the outside 210 of the insert (this specified maximum height increase may also be, for example, in the range of from one-sixteenth to six-sixteenths of an inch) and specifies the area of the ramp correction (this specified area may also range from a localized portion of the support surface of the insert to the entire support surface). In response to this instruction central processing unit 162 determines the required ramp correction from the specified maximum height increase at the outside 210 of the custom-made shoe insert 206 to a zero increase at the inside 208 of the insert and stores in random access memory 170 additional information for modifying the stored data record in the specified area in accordance with the required ramp correction.

The insert thickness adjustment compensates for slight differences of leg length or for shoe variations by modifying the stored data record as required to increase or decrease the thickness of the entire custom-made shoe insert 206 of FIG. 8 by a constant amount. As a part of the instruction for initiating the insert thickness adjustment, the operator specifies the desired minimum thickness of the custom-made shoe insert 206 (this specified minimum thickness may be, for example, in the range of from one-sixteenth to eight-sixteenths of an inch and is normally two-sixteenths of an inch). In response to this instruction central processing unit 162 determines the lowest data point (or height) recorded in the stored data record, thereupon determines a required constant height adjustment, and then stores in random access memory 170 additional information for modifying the entire stored data record in accordance with that constant height adjustment.

The pad/depression selection and placement adjustment provides metatarsal support and/or compensates for bunions, heel spurs and other such defects by modifying the stored data record as required to form the custom-made shoe insert 206 of FIG. 8 with one or more built-in pads and/or depressions appropriately shaped, sized and placed to provide the desired metatarsal support and/or compensate for any bunions, heel spurs or other such defects. Thus, any of the standard or custom-made pads employed by podiatrists, such as metatarsal pads (used for adjusting the load of any metatarsal by increasing and/or decreasing the load of any of the neighboring metatarsals), bunion pads, heel spur pads, posting pads and wedging pads, can be selected and formed in the proper position as a built-in part of the custom-made shoe insert 206. By forming the custom-made shoe insert 206 with built-in depressions of appropriate shape, size and position it is also possible to compensate for temporary irritations such as bumps, blisters, bruises and other such sore spots and thereby eliminate or reduce any pressure applied to those sore spots. As a part of the instruction for initiating the pad/depression selection and placement adjustment, the operator specifies a pad or depression and the desired shape, size, position and thickness or depth of that pad or depression. In response to this instruction central processing unit 162 stores in random access memory 170 additional information for modifying the stored data record in accordance with the specified shape, size, position and thickness or depth of the specified pad or depression.

The overall arch support adjustment compensates for arch problems, such as fallen arches, by modifying the stored data record as required to increase or decrease the height of the arch support provided by the custom-made shoe insert 206 of FIG. 8 by a selected percentage of the height of that support. As a part of the instruction for initiating the overall arch support adjustment, the operator specifies a desired data point in the arch of the foot as recorded in the stored data record and specifies the desired increase or decrease in height of that data point. In response to this instruction central processing unit 162 determines the percentage increase or decrease in height represented by the specified increase or decrease in height and stores in random access memory 170 additional information for modifying the entire stored data record in accordance with that percentage increase or decrease in height.

Figure 9:
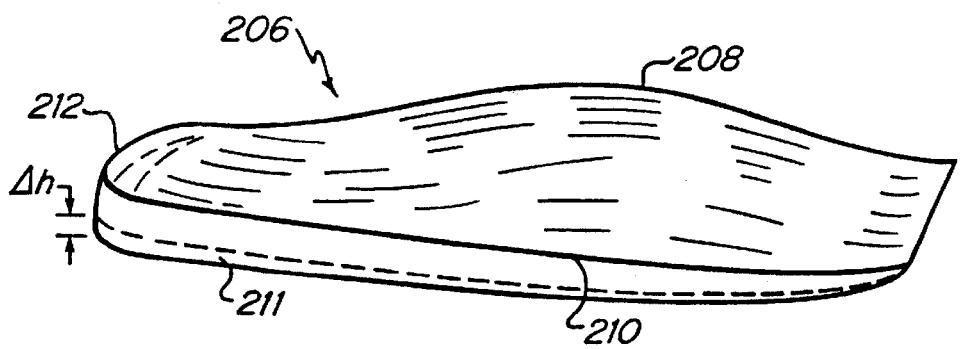
FIG. 9 is a perspective view of the custom-made shoe insert of FIG. 8 when shortened in length in accordance with a data record modification feature of the present invention.

The heel lift ramp adjustment, like the insert thickness adjustment, may be employed to compensate for slight differences of leg length, but does so by modifying the stored data record as required to increase the height of the heel portion of the custom-made shoe insert 206 without increasing the height of the metatarsal and toe portions, as indicated by the region 211 defined between the lowermost solid line and the dashed line in FIGS. 8 and 9. This has the advantage that there is no loss of toe space. As a part of the instruction for initiating the heel lift ramp adjustment the operator specifies the desired maximum increase in the height $\Delta h$ of the custom-made shoe insert 206 at the end 212 of the heel of the insert (this specified maximum height increase may be, for example, in the range of from one-sixteenth to six-sixteenths of an inch) and specifies the area of the ramp correction (this specified area may range from only the heel portion of the support surface of the insert to three-quarters of the entire support surface). In response to this instruction central processing unit 162 determines the required ramp correction from the specified maximum height increase $\Delta h$ at the end 212 of the heel of the custom-made shoe insert 206 to a zero increase at the opposite end of the specified area and stores in random access memory 170 additional information for modifying the stored data record in the specified area in accordance with the required ramp correction.

The toe crest or sulcus limit adjustment provides a less confining fit by modifying the stored data record as required to reduce or remove the toe crest or sulcus that is defined between the metatarsals and the toes and that would otherwise be formed in the custom-made shoe insert 206 of FIG. 8. This modification is not desired by many people who prefer the more-snug and better-grip fit provided by forming the custom-made shoe insert 206 with the full toe crest or sulcus 214. As a part of the instruction for initiating the toe crest or sulcus limit adjustment, the operator specifies the maximum desired toe crest or sulcus height, as measured from the lowest data point (or height) recorded in the arch-to-toe half of the stored data record (this specified maximum toe crest or sulcus height may be in the range of from zero to six-sixteenths of an inch). In response to this instruction central processing unit 162 determines the lowest data point (or height) recorded in the arch-to-toe half of the stored data record and thereupon stores in random access memory 170 additional information for modifying that half of the stored data record from that data point forward as necessary to limit the maximum thickness of the corresponding portion of the custom-made shoe insert 206 to the sum of the specified maximum toe crest or sulcus height and the determined lowest data point (or height).

The insert length adjustment is employed for informing the operator to reduce the length of the custom-made shoe insert 206 of FIG. 8 to any desired size, as shown, for example, in FIG. 9. This may be necessary for certain tight-fitting shoes. As a part of the instruction for initiating the insert length adjustment the operator specifies a desired amount by which the custom-made shoe insert 206 should be shortened after it has been shaped. This specified amount may be, for example, one-fourth full size, one-half full size, or three-fourths full size (orthotic size). In response to this instruction central processing unit 162 stores in random access memory 170 additional information for modifying the stored data record as necessary to prompt the operator, once the custom-made shoe insert 206 has been shaped, regarding the specified amount by which the custom-made shoe insert is to be shortened and to require an acknowledgement of that prompt by the operator.

Following each of the foregoing data record modification operations, central processing unit 162 causes display monitor 164 to display a message indicating completion of that operation and prompting the operator to enter the next instruction into computer 86 to initiate any further desired data record modification operation or a recording operation (hereinafter described). As an aid in performing each desired data record modification operation, central processing unit 162 may be employed for causing display monitor 164 to display contour lines providing a three-dimensional representation of the custom-made shoe insert 206 as defined by the stored data record following the foregoing scanning operation and as defined by both the stored data record and the stored additional information for modifying that data record following each desired data record modification operation. This is especially helpful in enabling the operator to properly place any desired pads and/or depressions during the pad/depression selection and placement adjustment operation and in enabling the operator to see the results of any desired data record modification operation just performed.

Once the last of the foregoing scanning and any desired data record modification operations has been completed, central processing unit 162, as noted above, causes display monitor 164 to display a message indicating completion of that operation and prompting the operator to enter the next instruction into computer 86. At this point the person's left foot 12 is properly positioned on the foot impression unit 10, as previously explained and as shown in FIG. 1. The operator may then repeat the impression-forming, the locking, the scanning and any desired data record modification operations, as previously described, for the person's left foot. Upon completion of the last of these operations the information for identifying the person, etc., the data record for the person's right foot and any additional information for modifying that data record, and the data record for the person's left foot and any additional information for modifying that data record are stored as a file in random access memory 170.

Once the last of these operations has been completed, central processing unit 162 causes display monitor 164 to display a message indicating completion of that operation and prompting the operator to enter the next instruction into computer 86. The operator may then employ keyboard input unit 160 for entering into computer 86 an instruction to record the aforementioned file on a floppy disc. In response to this instruction central processing unit 162 causes the aforementioned file then stored in random access memory 170 to be recorded on a floppy disc by floppy disc storage unit 172. It should be noted that this recording operation may be performed following any of the foregoing scanning and data record modification operations to record whatever portion of the aforementioned file may then be stored in random access memory 170 on a floppy disc and, as previously described, is performed following the calibration operation to record the aforementioned reference record on a floppy disc.

Figure 11:
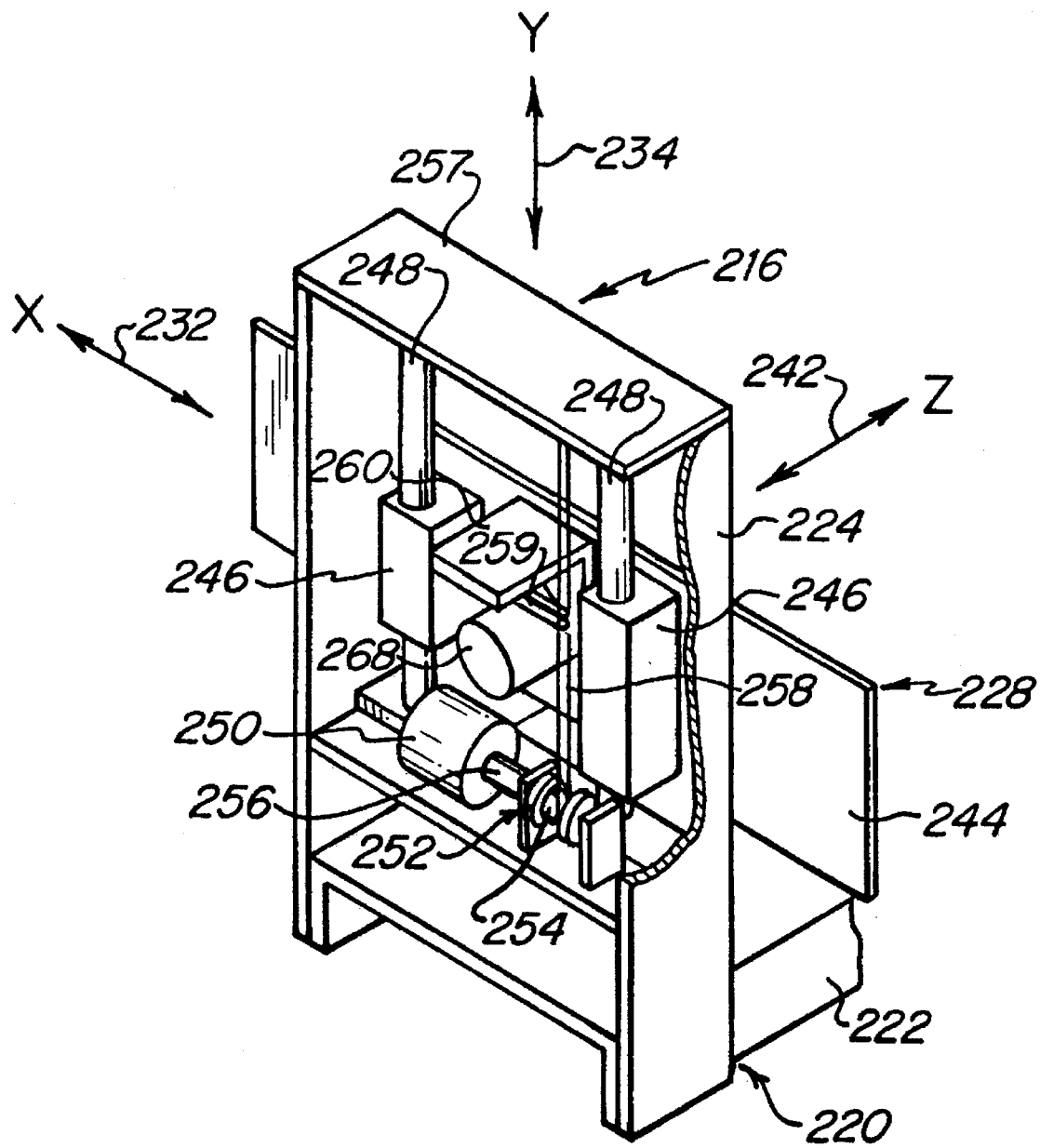
FIG. 11 is a partially cut away rear perspective view of a portion of the shaping unit of FIG. 10.
Figure 10:
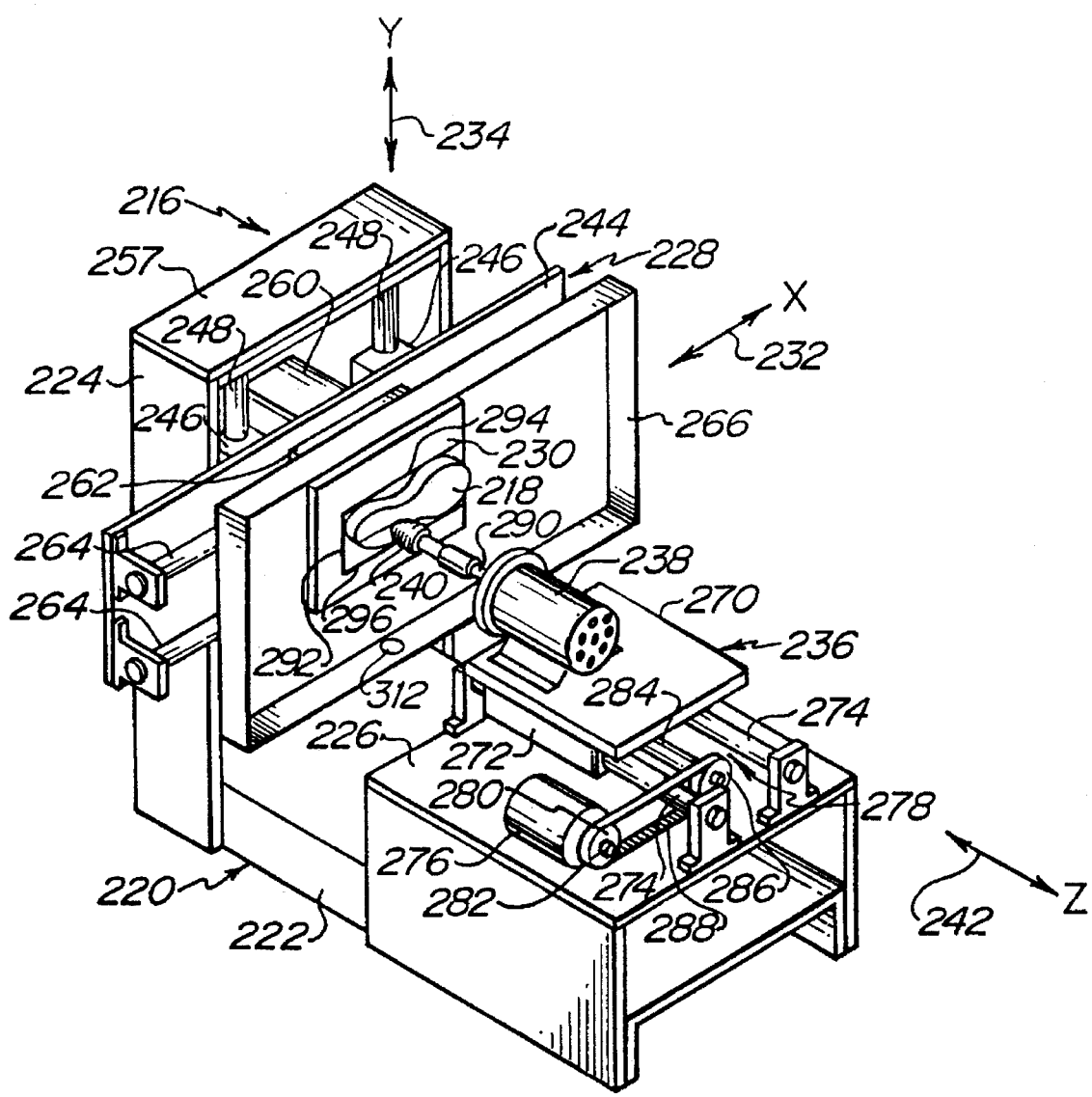
FIG. 10 is a front perspective view of a shaping unit for use in forming custom-made shoe inserts conforming to a digital representation of a person's foot provided by the foot impression unit of FIGS. 1–7.

The data record for each foot and any corresponding additional information for modifying that data record, as then stored in random access memory 170 and recorded on the floppy disc, may then be employed for controlling a shaping unit 216, as shown in FIGS. 10 and 11, to shape an insert blank 218 in accordance with that data record and corresponding additional information and thereby form a custom-made shoe insert 206, as shown, for example, in FIG. 8 or 9, conforming to the undersurface of the foot. This may be done at a customer or patient service location where the previously described operations are performed or it may be done at another shaping location supporting a number of customer or patient service locations. In the latter case the floppy disc is mailed or otherwise delivered to the shaping location or the aforementioned file recorded on the floppy disc is electronically transmitted to the shaping location.

Referring now to FIGS. 10 and 11, the shaping unit 216 may comprise, for example, a conventional milling machine or, as illustrated, a simplified version of same including a frame 220 having a base 222, an upright support structure 224 fixedly attached to the base at one end thereof, and a platform 226 fixedly attached to the base at the opposite end thereof. The shaping unit 216 also includes an X-Y stage 228 supported by the upright support structure 224 for moving a blank-mounting plate 230 from side to side along an X axis 232 and up and down along a Y axis 234, and a Z-axis stage 236 supported by the platform 226 for moving a high-speed shaping motor 238 and an associated hemispherical cutter 240 in and out along a Z axis 242 perpendicular to the blank mounting plate.

The X-Y stage 228 includes a Y-axis plate 244 fixedly attached to a pair of bearing members 246, which are in turn slidably mounted on a pair of parallel vertical shafts 248 fixedly attached to the upright support structure 224. Additionally, the X-Y stage 228 includes a Y-axis stepper motor 250 fixedly mounted on the upright support structure 224 and coupled to the Y-axis plate 244 by a capstan drive mechanism 252. This capstan drive mechanism 252 includes a pulley 254 fixedly secured to drive shaft 256 of the Y-axis stepper motor 250, another pulley (not shown) rotatably suspended from the top 257 of upright support structure 224, and a cable 258 that is secured at both ends to a member 259 protruding from an L-shaped bracket 260 fixedly attached to Y-axis plate 244 and that is arranged to wrap and unwrap on these pulleys under control of the Y-axis stepper motor as required to move the Y-axis plate up and down along the Y axis 234.

The X-Y stage 228 also includes an X-axis plate 262 fixedly attached to a pair of bearing members (not shown, but similar to bearing members 246), which are in turn slidably mounted on a pair of parallel horizontal shafts 264 fixedly attached to Y-axis plate 244. A particle containment tray 266 with a transparent cover (not shown) having a centrally disposed clearance opening is fixedly attached to X-axis plate 262. Blank-mounting plate 230 is releasably secured to particle containment tray 266 at a predetermined centrally-disposed mounting position and is readily accessible through the clearance opening of the aforementioned transparent cover to facilitate the release and removal of the blank-mounting plate and its subsequent return and re-securing to the particle containment tray at the predetermined mounting position. This helps in properly mounting an insert blank 218 on blank-mounting plate 230 in preparation for shaping the blank to form a custom-made shoe insert 206, such as the one shown in FIG. 8, and in subsequently demounting the custom-made shoe insert. The insert blank 218 may be mounted on blank-mounting plate 230 by employing double-sided adhesive tape or by employing a vacuum clamping mechanism, both of which are described in the aforementioned U.S. Pat. No. 4,454,618 and 4,510,636.

The X-Y stage 228 further includes an X-axis stepper motor 268, which is fixedly mounted on the L-shaped bracket 260 attached to Y-axis plate 244, and which is coupled to X-axis plate 262 through clearance openings in the L-shaped bracket and the Y-axis plate by a drive mechanism (not shown, but similar to capstan drive mechanism 252 or to a lead-screw drive mechanism as hereinafter described in connection with the Z-axis stage 236). Under control of X-axis stepper motor 268 this drive mechanism moves X-axis plate 262 and the attached particle containment tray 266 from side to side along the X-axis 232. Thus, when blank-mounting plate 230 is secured to particle containment tray 266, the blank-mounting plate and, hence, an insert blank 218 mounted thereon may be moved up and down along the Y-axis 234 under control of Y-axis stepper motor 250 and from side to side along the X axis 232 under control of X-axis stepper motor 268.

The Z-axis stage 236 includes a Z-axis plate 270 fixedly attached to a pair of bearing members 272, which are in turn slidably mounted on a pair of parallel horizontal shafts 274 fixedly attached to platform 226. Additionally, the Z-axis stage 236 includes a Z-axis stepper motor 276 fixedly mounted on platform 226 and coupled to Z-axis plate 270 by a lead-screw drive mechanism 278. This drive mechanism 278 includes a pulley 280 fixedly attached to drive shaft 282 of Z-axis stepper motor 276, a lead screw 284 rotatably and threadably coupled at one end to Z-axis plate 270, another pulley 286 fixedly attached to the other end of the lead screw, and a continuous belt 288 engaged with these pulleys to rotate the lead screw. Under control of Z-axis stepper motor 276 drive mechanism 278 moves Z-axis plate 270 in and out along the Z axis 242.

Shaping motor 238 is fixedly mounted on Z-axis plate 270 for movement therewith along the Z axis 242. Concomitantly, hemispherical cutter 240, which, for example, has a carbide surface and a diameter of 1.0 inch, is fixedly secured to drive shaft 290 of shaping motor 238 for high-speed rotation to remove material from the insert blank 218 mounted on blank-mounting plate 230. Shaping motor 238 may be mounted such that its drive shaft 290 is disposed at an angle of, for example, twenty degrees from the Z axis 242 towards either the X axis 232 or the Y axis 234 to allow hemispherical cutter 240 to more effectively remove material from the insert blank 218.

Figure 12:
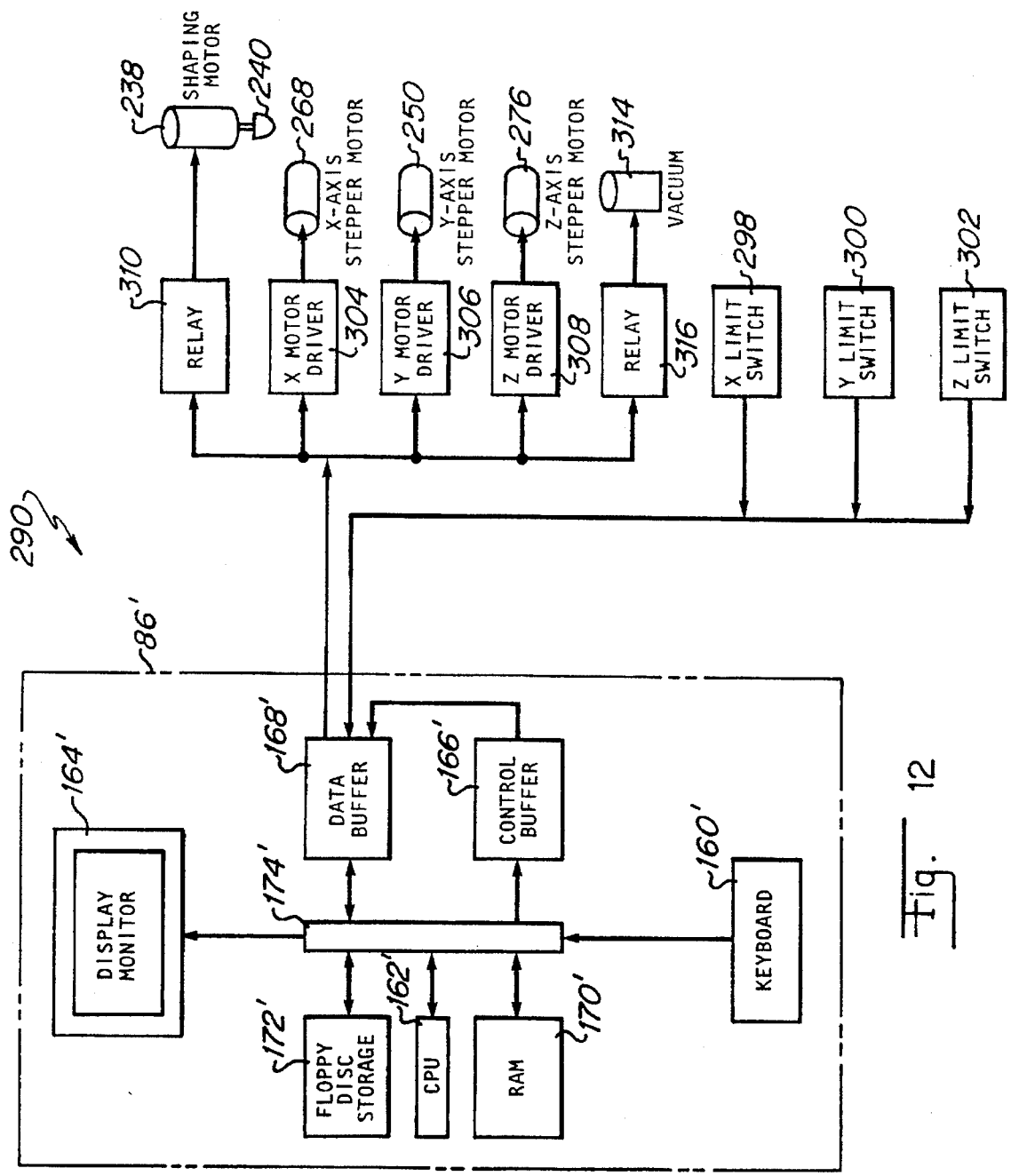
FIG. 12 is a block diagram of a control system for use with the shaping unit of FIGS. 10 and 11.

Referring now to FIG. 12, there is shown a control system 290 for operating the shaping unit 216 of FIGS. 10 and 11 to produce a custom-made shoe insert 206, as shown, for example, in FIG. 8, for each of the person's feet 12. This control system includes a computer 86', which may be the same computer 86 employed in the control system 156 for operating the foot impression unit 10 (particularly when the shaping unit 216 is located at the same customer or patient service location as the foot impression unit) or another computer of the same type (particularly when the shaping unit is located at another shaping location). Since in either case such a computer 86 and its various components have already been described in connection with the control system 156 for the foot impression unit 10, the same reference numbers previously used to designate that computer and its components have been used and primed to designate the computer 86' and its various components in the following description of the control system 290 for the shaping unit 216.

Assuming, for example, that the shaping unit 216 and the control system 290 therefor are located at a central shaping location and that a floppy disc containing the person's previously recorded file has been delivered to that location, the operator initially inserts the floppy disc into floppy disc storage unit 172' of computer 86' and employs keyboard input unit 160' for instructing central processing unit 162' to store the person's previously recorded file in random access memory 170' of the computer. The operator may then employ keyboard input unit 160' for instructing central processing unit 162' to cause display monitor 164' to display the identification information portion of that stored file. This identifies the name, address, shoe size, etc. of the person for whom a pair of custom-made shoe inserts 206, such as the one shown in FIG. 8, is to be formed in accordance with the remaining portions of the stored file (namely, the data record portions for the person's right and left feet and any corresponding additional information portions for modifying those data record portions).

At this point the operator mounts an insert blank 218 of appropriate size for the person's right foot 12 on blank mounting plate 230 in the position defined by a vertical reference line 292 and an uppermost horizontal reference line 294, as shown in FIG. 11. The vertical reference line 292, the uppermost horizontal reference line 294, and a lowermost horizontal reference line 296 formed on blank-mounting plate 230 correspond to the end guide member 52, the first side guide member 54, and the second side guide member 56, respectively, of the foot impression unit 10 (see FIG. 1) and are employed in the same manner to properly position the insert blank 218 for the person's right foot 12 and to subsequently properly position another insert blank for the person's left foot.

Once the insert blank 218 for the person's right foot 12 has been properly mounted on blank-mounting plate 230, the operator employs keyboard input unit 160' for entering into computer 86' an instruction to move hemispherical cutter 240 to a home position for the person's right foot 12. This home position is located adjacent to the junction of the vertical and uppermost reference lines 292 and 294 at X, Y and Z coordinates as defined by X, Y and Z limit switches 298, 300 and 302 disposed on blank shaping unit 216 so as to detect the X-axis, Y-axis and Z-axis plates 262,244 and 270, respectively, when hemispherical cutter 240 is in the home position. In response to the last-mentioned instruction central processing unit 162' causes control buffer unit 166' to activate data buffer unit 168' for transmitting control data and for receiving control signals from the X, Y and Z limit switches 298, 300 and 302 and causes the activated data buffer unit to transmit control data to X, Y and Z motor driver's 304, 306 and 308 as required for causing the X-axis, Y-axis and Z-axis stepper motors 268, 250 and 276 to step hemispherical cutter 240 to the home position for the person's right foot. Once hemispherical cutter 240 is in that home position, the X, Y and Z limit switches 298, 300 and 302 produce control signals, which are received by the activated data buffer unit 168', and which thereupon cause central processing unit 162' to halt the stepping of the hemispherical cutter.

Following completion of the foregoing home-positioning operation, the operator employs keyboard input unit 160' for entering into computer 86' an instruction to shape the insert blank 218 for the person's right foot 12 in accordance with the corresponding portion or portions of the stored file (namely, the data record portion for the person's right foot and any corresponding additional information for modifying that data record portion). In response to this instruction central processing unit 162' causes control buffer unit 166' to activate data buffer unit 168' for transmitting control data and causes the activated data buffer unit to transmit control data to a relay 310 as required for energizing shaping motor 238 to rotate hemispherical cutter 240 at high speed. Central processing unit 162' also causes the activated data buffer unit to transmit control data to the X, Y and Z motor drivers 304, 306 and 308 as required for driving the X-axis, Y-axis and Z-axis stepper motors 268, 250 and 276 to step hemispherical cutter 240 along the X axis 232 in steps of 0.01 inch (a thirty-second of the center-to-center spacing of gauging elements 34), along the Y axis 234 in steps of 0.08 inch (a fourth of the center-to-center spacing of the gauging elements), and along the Z axis 242 in steps of 0.0025 inch (half a vertical step of sensing mechanism 102). Moreover, central processing unit 162' processes the last-mentioned portion or portions of the stored file (namely, the data record portion for the person's right foot and any corresponding additional information portion for modifying that data record portion), taking into account the diameter of hemispherical cutter 240 and the stored level or height data for positions or steps corresponding to the positions of adjacent gauging elements 34, as required for causing the activated data buffer unit 168' to provide interpolated level or height control data for each intervening position or step in a curve-fitting manner.

Accordingly, hemispherical cutter 240 is stepped from the home position for the person's right foot to an initial position corresponding to the position of the first gauging element 34 in the first row of the array of gauging elements and thence forward along the X axis to 1023 successive additional positions the last of which corresponds to the position of the last gauging element in the same row (the initial and every thirty-second one of those positions corresponding to the positions of the successive gauging elements in that row). Hemispherical cutter 240 is then stepped downward along the Y axis 234 one step to another position and thence back along the X axis 232 to 1023 successive additional positions, is then stepped downward along the Y axis another step to another position and thence forward again along the X axis to 1023 successive additional positions, is then stepped downward along the Y axis still another step to still another position and thence back again along the X axis to 1023 successive additional positions, is then stepped downward along the Y axis a further step to a further position corresponding to the position of the first gauging element in the next row of gauging elements, etc. in a serpentine manner until the hemispherical cutter reaches a final position corresponding to the position of the last gauging element in the last row of gauging elements. At each position to which hemispherical cutter 240 is stepped, it is moved in and out along the Z axis 242 as determined by the level or height data stored in the last-mentioned portion or portions of the stored file (namely, the data record portion for the person's right foot 12 and any corresponding additional information portion for modifying that data record portion to compensate for any defects of that foot) or by the interpolated height or level control data. Thus, upon completion of the shaping operation the insert blank 218 is shaped to form a custom-made shoe insert 206, as shown, for example, in FIG. 8, conforming to the undersurface of the person's right foot, except as modified to compensate for any defects of that foot.

The particles of material removed from the insert blank 218 during the foregoing shaping operation are collected in particle containment tray 266 shown in FIG. 11. In order to facilitate removal of these particles of material, the particle containment tray 266 is provided with an outlet port 312 in the vicinity of hemispherical cutter 240. The outlet port 312 is coupled to a source of vacuum 314 for sucking the particles of material from particle containment tray 266 into a waste disposal tank (not shown). Thus, at the outset of the shaping operation central processing unit 162' also causes data buffer unit 168' to transmit control data to another relay 316 as required for energizing the source of vacuum 314 to remove particles of material from particle containment tray 266.

The foregoing home-positioning and shaping operations are repeated for the person's left foot to similarly form a custom-made shoe insert 206 in accordance with the corresponding portion or portions of the stored file (namely, the data record portion for the person's left foot and any corresponding additional information portion for modifying that data record portion). However, it should be noted that the home position for the left foot 12 is located adjacent to the junction of the vertical and lowermost reference lines 292 and 296 and is determined by central processing unit 162' based on the home position defined for the right foot by the X, Y and Z limit switches 298, 300 and 302. The resulting pair of custom-made shoe inserts 206 may be inserted into a pair of the person's own shoes, thereby customizing those shoes, or may be used in forming a pair of custom-made shoes for the person.

We claim:

1. Apparatus for digitizing the contour of the undersurface of a person's foot, said apparatus comprising:
   an array of gauging elements supported by a support structure and disposed in spaced relationship for independently guided movement along longitudinal axes of the gauging elements towards the undersurface of the person's foot, each of said gauging elements including an activating portion for allowing the position of each gauging element to be detected;
   first control means for urging the gauging elements along said longitudinal axes into extended positions in contact with the undersurface of the person's foot;
   sensor means disposed adjacent to the array of gauging elements for scanning the gauging elements to produce digital signals indicative of the positions of the gauging elements, said sensor means including an array of sensors supported by a support structure and disposed with each sensor adjacent to a corresponding gauging element;
   second control means for producing relative movement between the array of gauging elements and the array of sensors while the gauging elements are in the extended positions to which they are urged by the first control means so as to enable the sensors to sense the activating portions of the corresponding gauging elements and produce digital signals indicative of the positions of the gauging elements; and
   storage means, coupled to the sensor means, for storing the digital signals therefrom to provide a digital representation of the undersurface of the person's foot.

2. Apparatus as in claim 1 wherein said storage means comprises computer means, coupled to the sensor means, for storing and processing the digital signals indicative of the positions of the gauging elements to provide the digital representation of the undersurface of the person's foot.

3. Apparatus as in claim 1 wherein said computer means is operable for modifying the digital representation of the undersurface of the person's foot to compensate for a defect of the person's foot.

4. Apparatus as in claim 1 including locking means for holding said gauging elements in place in the extended positions to which they are urged by the first control means.

5. Apparatus as in claim 1 wherein:
   the activating portion of each of said gauging elements comprises a magnetic activator; and
   each of said sensors comprises a Hall-effect sensor for detecting the magnetic activator of the corresponding gauging element.

6. Apparatus as in claim 1 including:
   holding means for holding a blank of material from which a custom-made shoe insert is to be formed; and
   shaping means, responsive to the digital representation of the undersurface of the person's foot, for shaping the blank to provide the custom-made shoe insert in conformance with that digital representation.

7. Apparatus for digitizing the contour of the undersurface of a person's foot, said apparatus comprising:
   an array of gauging elements supported by a support structure and disposed in spaced relationship for independently guided movement along longitudinal axes of the gauging elements towards the undersurface of the person's foot, each of said gauging elements including an activating portion for allowing the position of each gauging element to be detected;
   a control mechanism for urging the gauging elements along said longitudinal axes into extended positions in contact with the undersurface of the person's foot;
   an array of sensors, supported by a support structure and disposed with each sensor adjacent to a corresponding gauging element, for scanning the gauging elements to produce digital signals indicative of the positions of the gauging elements;
   a control mechanism for producing relative movement between the array of gauging elements and the array of sensors while the gauging elements are in the extended positions so as to enable the sensors to sense the activating portions of the corresponding gauging elements and produce digital signals indicative of the positions of the gauging elements; and
   a storage device, coupled to the array of sensors, for storing the digital signals therefrom to provide a digital representation of the undersurface of the person's foot.

8. Apparatus as in claim 7 wherein said storage device comprises a computer, coupled to the array of sensors, for storing and processing the digital signals indicative of the positions of the gauging elements to provide the digital representation of the undersurface of the person's foot.

9. Apparatus as in claim 8 wherein said computer is operable for modifying the digital representation of the undersurface of the person's foot to compensate for a defect of the person's foot.

10. Apparatus as in claim 7 including a locking mechanism for holding said gauging elements in place in the extended positions to which they are urged.

11. Apparatus as in claim 7 wherein:
    the activating portion of each of said gauging elements comprises a magnetic activator; and
    each of said sensors comprises a Hall-effect sensor for detecting the magnetic activator of the corresponding gauging element.

12. Apparatus for digitizing the undersurface of the person's foot, said apparatus comprising:
    a digitizer for scanning the undersurface of the person's foot to produce digital signals indicative of the contour of the undersurface of the person's foot; and a digital processor, coupled to said digitizer, for storing and processing said digital signals to provide a digital representation of the undersurface of the person's foot;

said digital processor being adapted for modifying the digital representation of the undersurface of the person's foot to compensate for a characteristic of the person's foot.

13. Apparatus as in claim 12 including a shaping mechanism for shaping a blank of material in accordance with the modified digital representation of the undersurface of the person's foot to form a custom-made shoe insert providing compensation for the characteristic of the person's foot.

* * * * *